(12) United States Patent
Suzuki

(10) Patent No.: US 10,709,453 B2
(45) Date of Patent: Jul. 14, 2020

(54) IN VIVO INDWELLING MEMBER AND METHOD FOR PRODUCING SAME

(71) Applicant: KANEKA CORPORATION, Osaka-shi, Osaka (JP)

(72) Inventor: Shohei Suzuki, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 569 days.

(21) Appl. No.: 15/312,455

(22) PCT Filed: May 14, 2015

(86) PCT No.: PCT/JP2015/063906
§ 371 (c)(1),
(2) Date: Nov. 18, 2016

(87) PCT Pub. No.: WO2015/178282
PCT Pub. Date: Nov. 26, 2015

(65) Prior Publication Data
US 2017/0105738 A1   Apr. 20, 2017

(30) Foreign Application Priority Data

May 19, 2014 (JP) ................................. 2014-103120

(51) Int. Cl.
 *A61B 17/12* (2006.01)
 *A61B 17/00* (2006.01)

(52) U.S. Cl.
 CPC .... *A61B 17/12113* (2013.01); *A61B 17/1214* (2013.01); *A61B 17/12031* (2013.01);
(Continued)

(58) Field of Classification Search
 CPC ........ A61B 17/12163; A61B 17/12113; A61B 17/12145; A61B 17/12031;
(Continued)

(56) References Cited

U.S. PATENT DOCUMENTS 5,645,558 A * 7/1997 Horton ............. A61B 17/12022
606/191
5,749,891 A * 5/1998 Ken ................. A61B 17/12022
606/200
(Continued)

FOREIGN PATENT DOCUMENTS

EP    0 765 636 A2   4/1997
JP      3024071 B2   3/2000
(Continued)

OTHER PUBLICATIONS

U.S. Pat. No. 5,766,219-A corresponds to JP 3665133-B2.
(Continued)

*Primary Examiner* — Tan-Uyen T Ho
*Assistant Examiner* — Chima U Igboko
(74) *Attorney, Agent, or Firm* — Birch, Stewart, Kolasch & Birch, LLP

(57) ABSTRACT

A method for producing an in vivo indwelling member having a secondary coil in which a secondary shape is given to a linear primary coil with a primary shape given to a linear material, includes: a first three-dimensional body formation step of forming a first three-dimensional body by aligning in a loop a plurality of segments, each of the segments being formed by winding the primary coil at least once, so that a part of the primary coil is spatially arranged; a second three-dimensional body formation step of forming a second three-dimensional body by aligning in a loop a plurality of segments, each of the segments being formed by winding the primary coil at least once, so that at least a part of the rest of the primary coil is spatially arranged after the formation of the first three-dimensional body; and an inside arrangement step of arranging one of the first and second three-dimensional bodies inside a loop part formed of the plurality
(Continued)

of segments aligned in a loop of the other three-dimensional body.

10 Claims, 12 Drawing Sheets

(52) U.S. Cl.
CPC ............... *A61B 17/12145* (2013.01); *A61B 2017/00526* (2013.01)

(58) Field of Classification Search
CPC ...... A61B 17/1214; A61B 2017/00526; A61B 17/12022; A61B 17/12027; A61B 17/12036; A61B 17/1204; A61B 17/12045; A61B 17/12131; A61B 17/1215; A61B 17/12168; A61B 17/12172; A61B 2017/12127; A61B 17/12154; A61B 17/12177
See application file for complete search history.

(56) References Cited

U.S. PATENT DOCUMENTS

| | | | |
|---|---|---|---|
| 5,766,219 A | 6/1998 | Horton | |
| 6,171,326 B1 | 1/2001 | Ferrera et al. | |
| 6,322,576 B1 * | 11/2001 | Wallace | A61B 17/12022 606/191 |
| 2005/0090855 A1 | 4/2005 | Ferrera et al. | |
| 2005/0192618 A1 | 9/2005 | Porter | |
| 2007/0175536 A1 * | 8/2007 | Monetti | A61B 17/12022 140/102.5 |
| 2009/0254112 A1 | 10/2009 | Gorospe et al. | |

FOREIGN PATENT DOCUMENTS

| | | |
|---|---|---|
| JP | 2003-230465 A | 8/2003 |
| JP | 2004-500929 A | 1/2004 |
| JP | 3665133 B2 | 6/2005 |
| JP | 2007-525304 A | 9/2007 |
| JP | 4065665 B2 | 3/2008 |
| JP | 2010-051475 A | 3/2010 |
| JP | 2010-517689 A | 5/2010 |

OTHER PUBLICATIONS

EP 0 765 636-A2 corresponds to JP 3024071-B2.
U.S. Pat. No. 6,171,326-B1 corresponds to JP 4065665-B2.
US 2005/0090855-A1 corresponds to JP 2004-500929-A.
US 2005/0192618-A1 corresponds to JP 2007-525304-A.
US 2009/0254112-A1 corresponds to JP 2010-517689-A.
International Search Report (PCT/ISA/210) issued in PCT/JP2015/063906, dated Jun. 23, 2015.
Written Opinion (PCT/ISA/237) issued in PCT/JP2015/063906, dated Jun. 23, 2015.

* cited by examiner

[Fig. 1A]
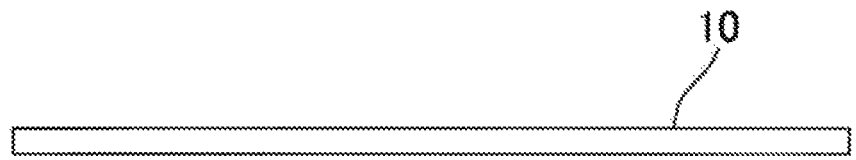
[Fig. 1B]
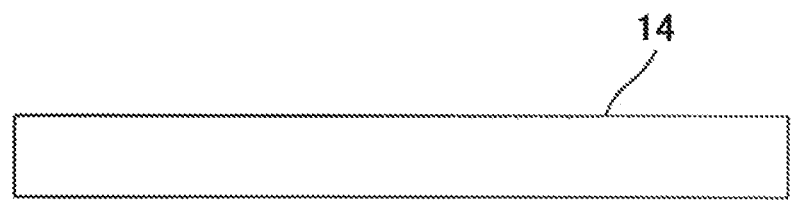
[Fig. 1C]
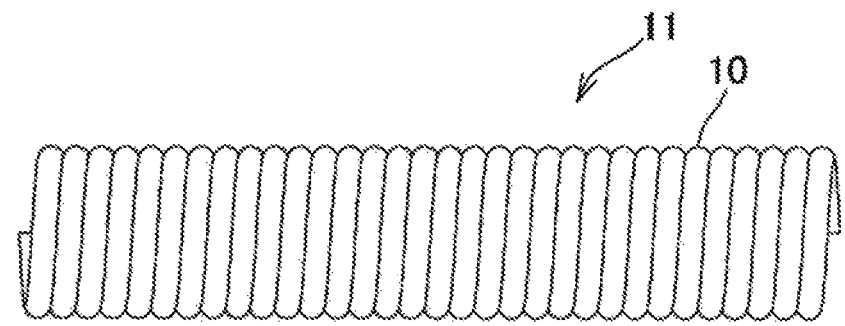
[Fig. 1D]
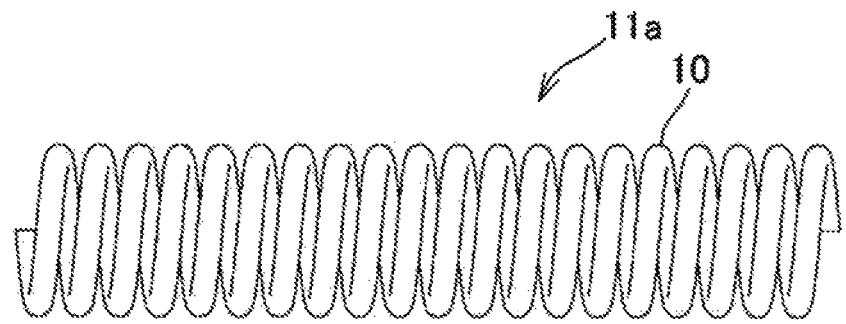

[Fig. 2A]
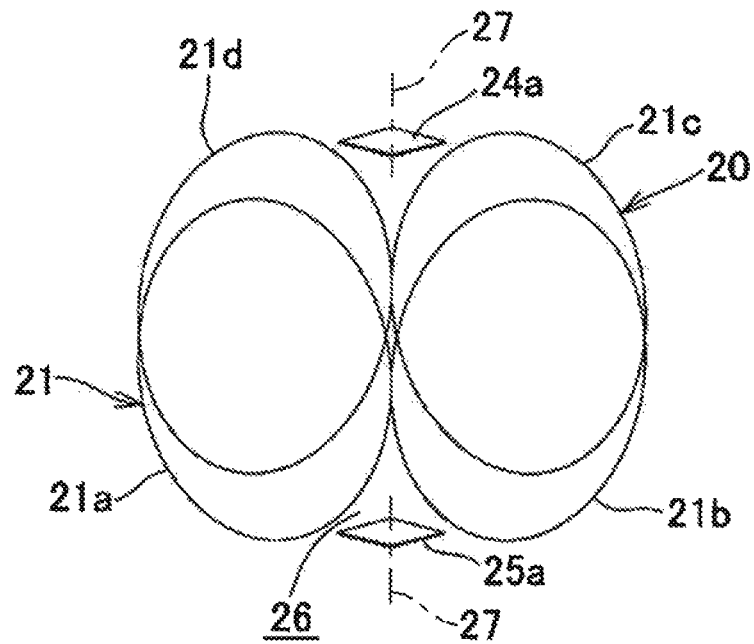
[Fig. 2B]
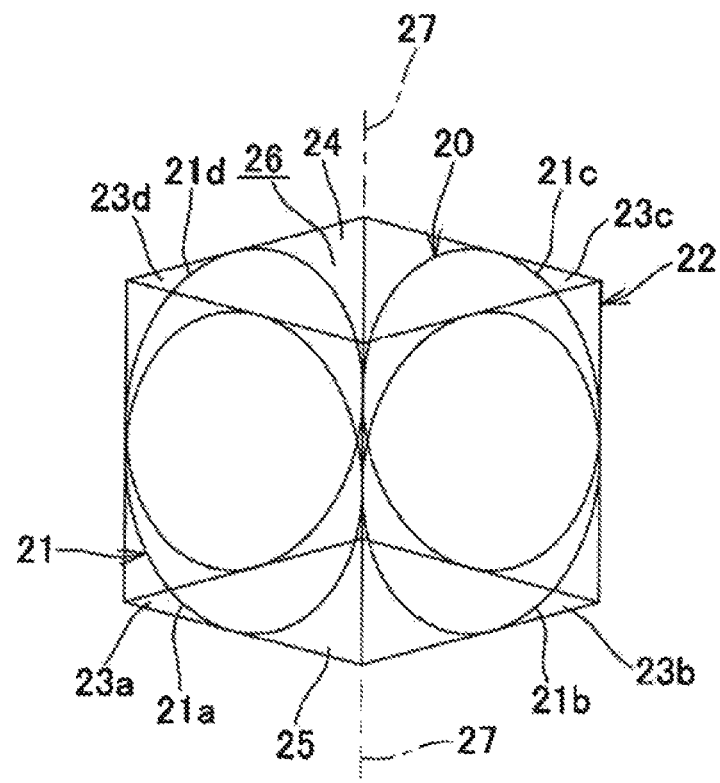

[Fig. 2C]
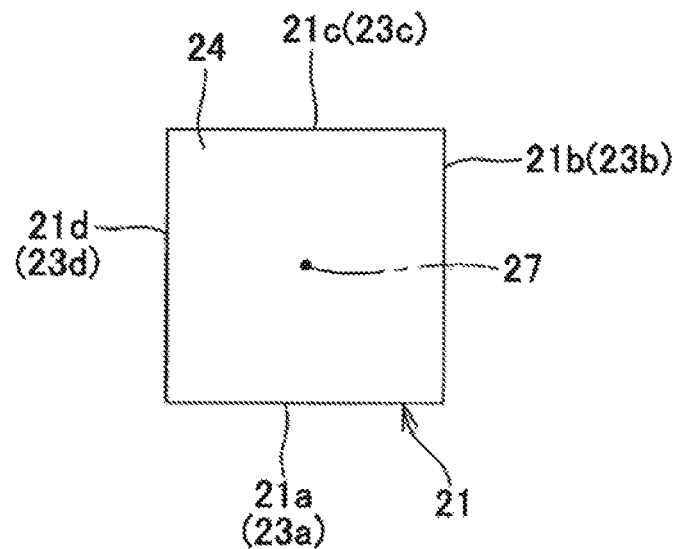
[Fig. 3]
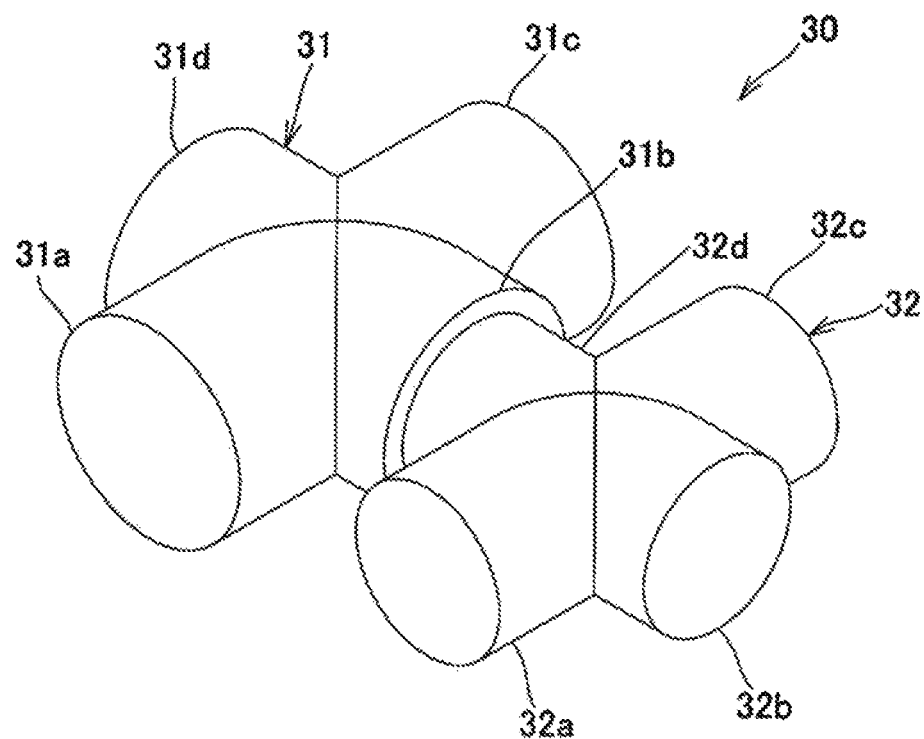

[Fig. 4]
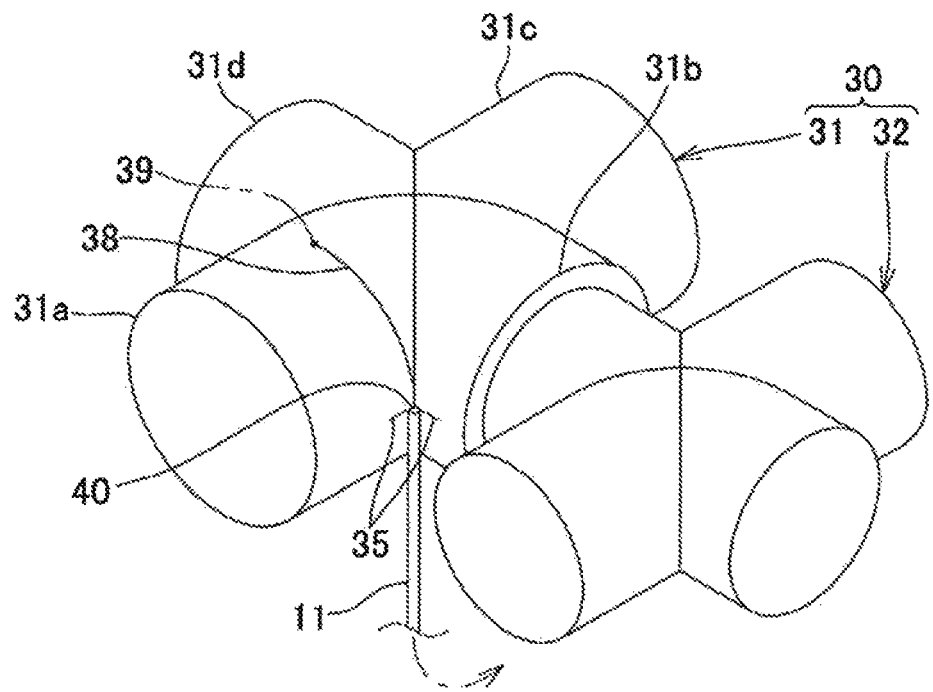
[Fig. 5]
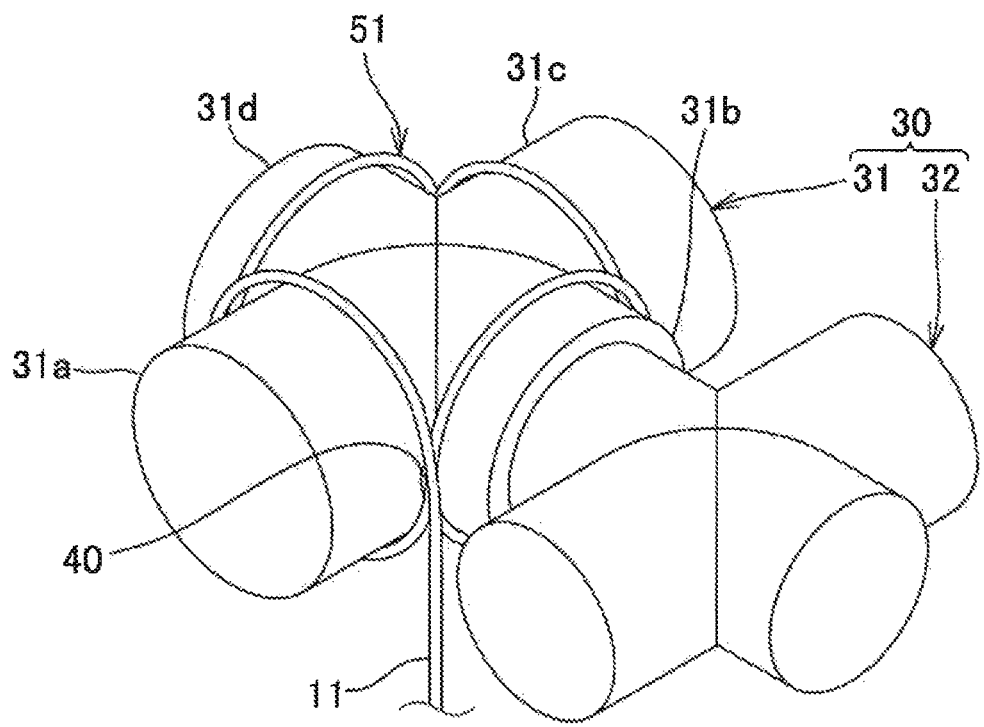

[Fig. 6]
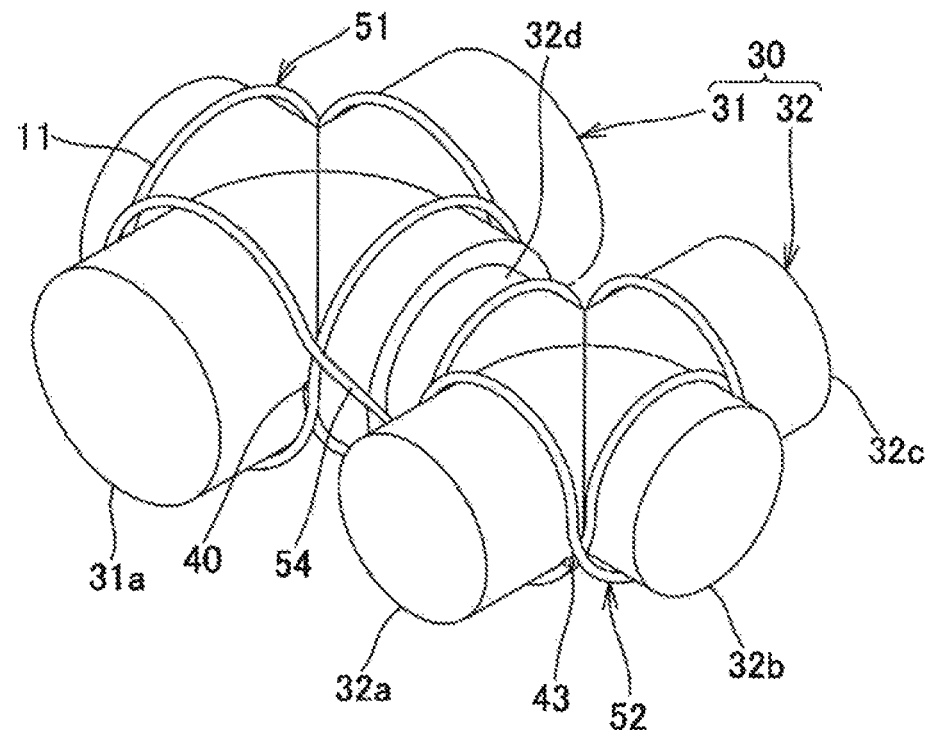
[Fig. 7A]
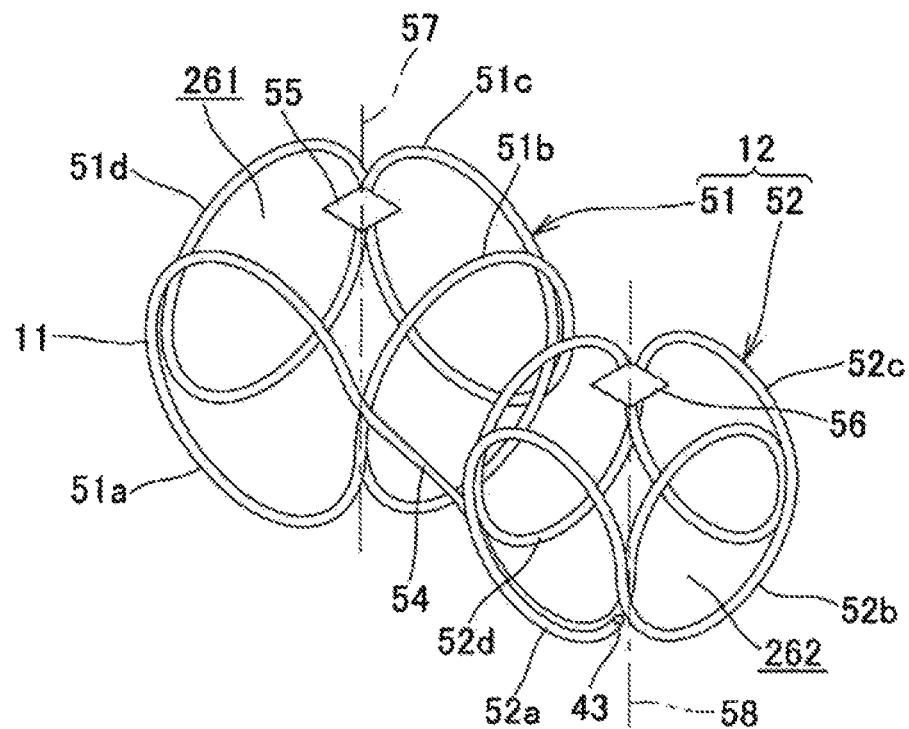

[Fig. 7B]
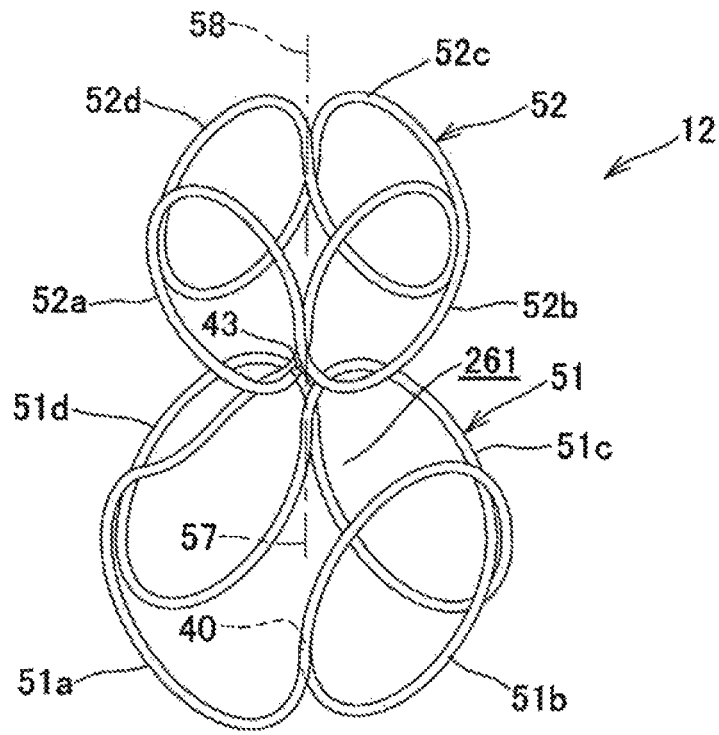
[Fig. 7C]
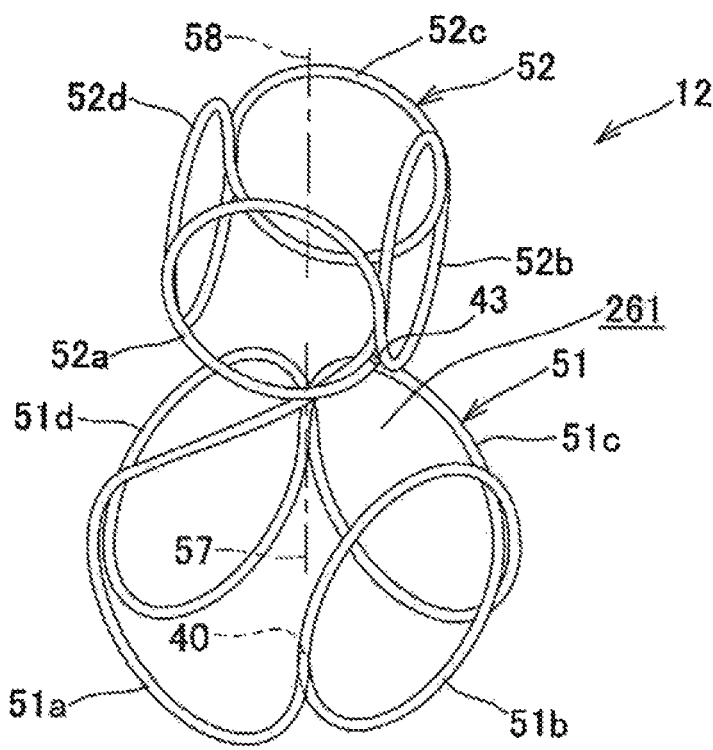

[Fig. 7D]
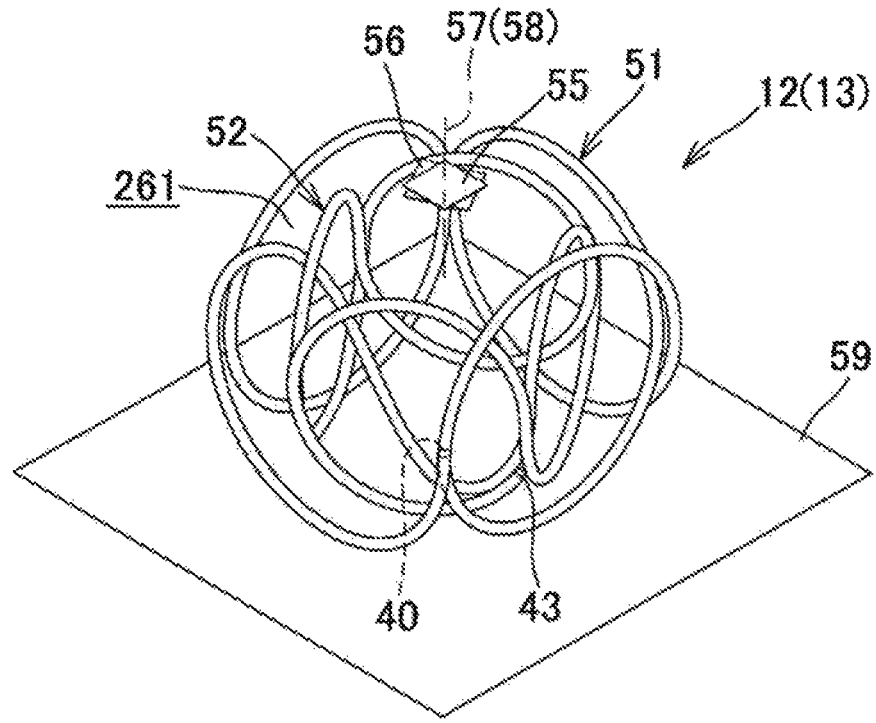
[Fig. 7E]
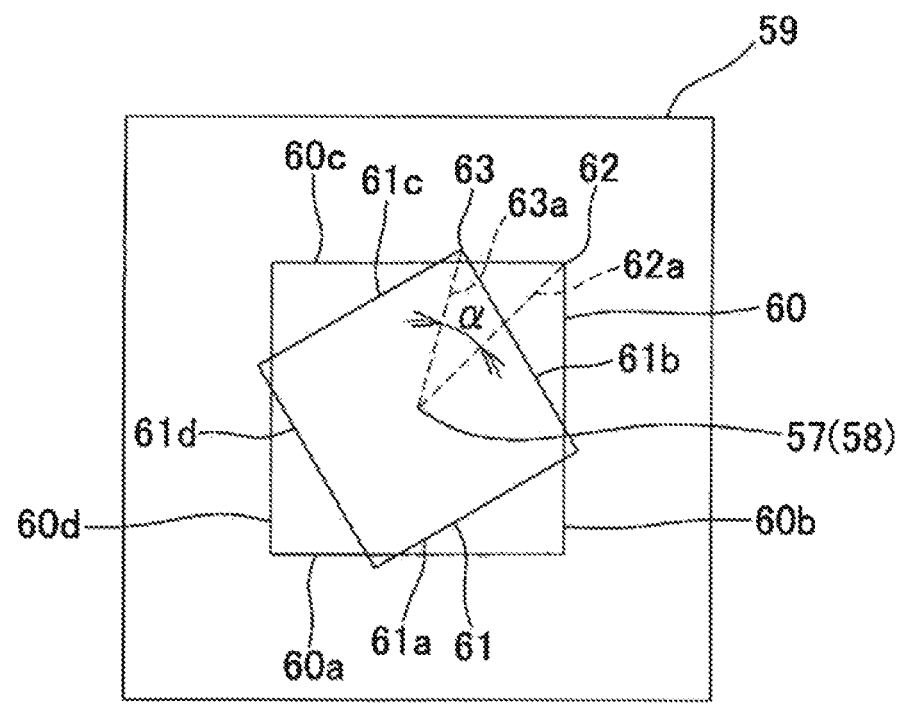

[Fig. 8A]
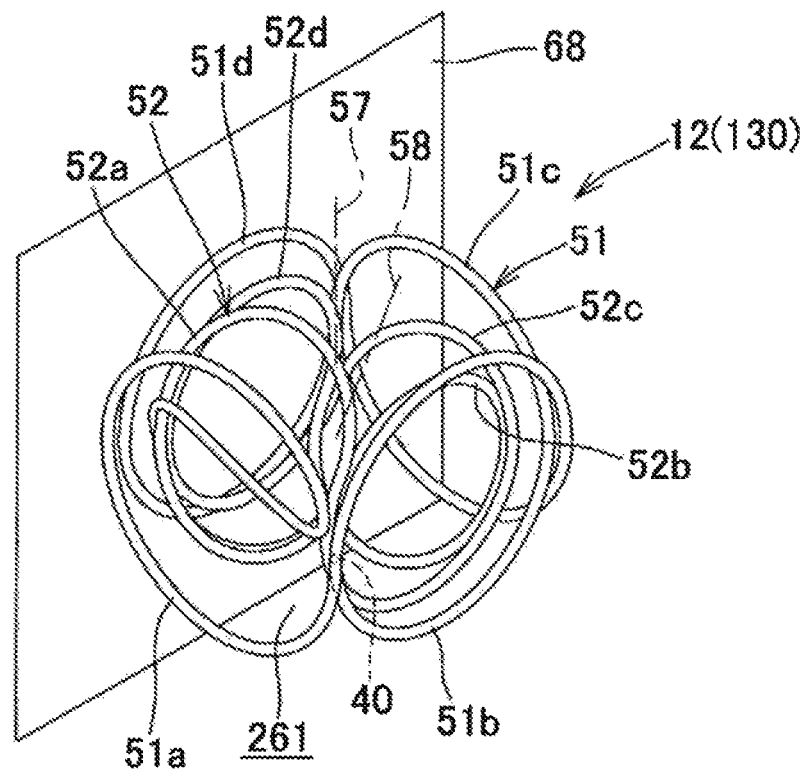
[Fig. 8B]
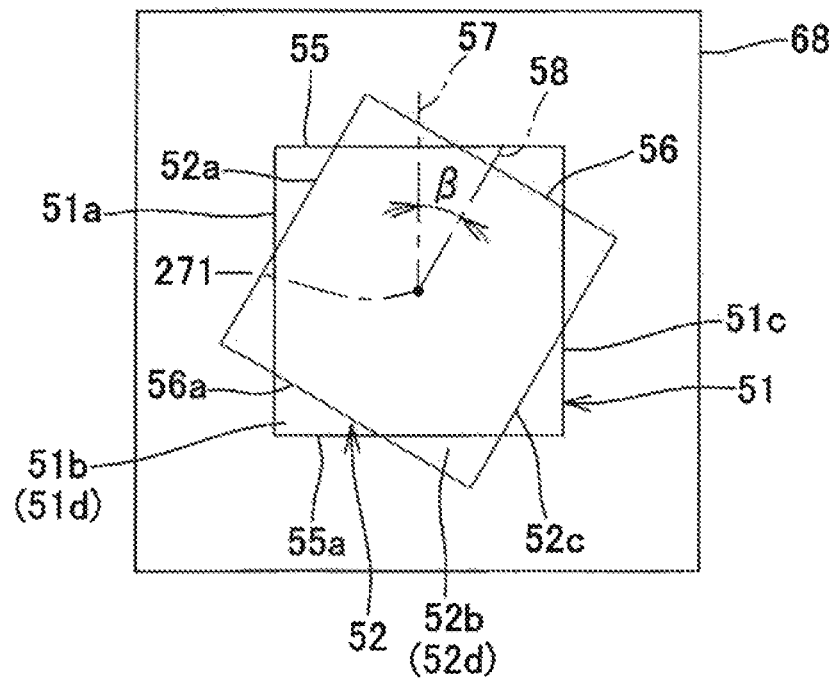

[Fig. 9]
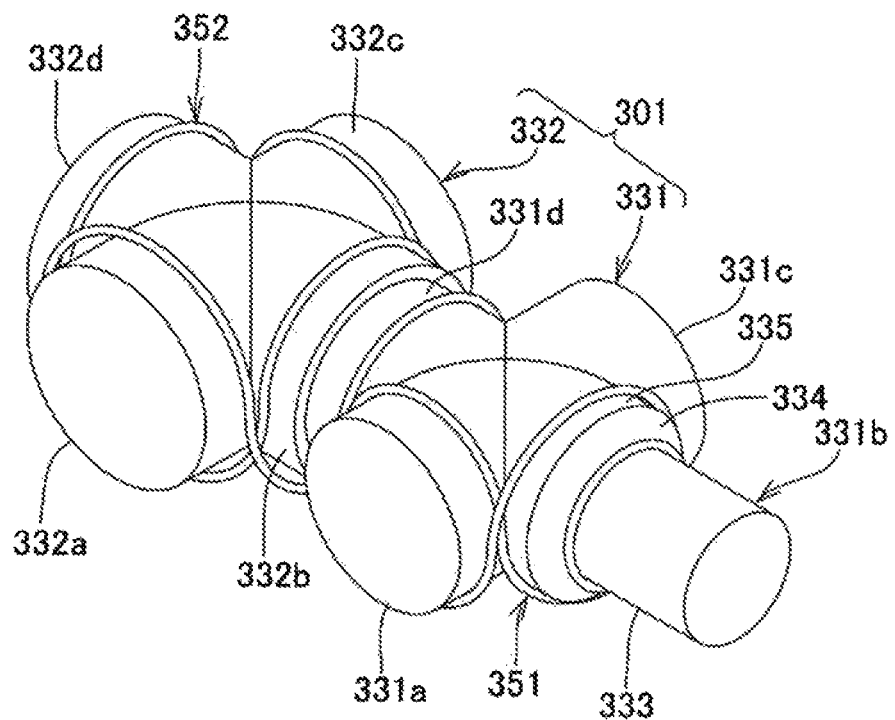
[Fig. 10]
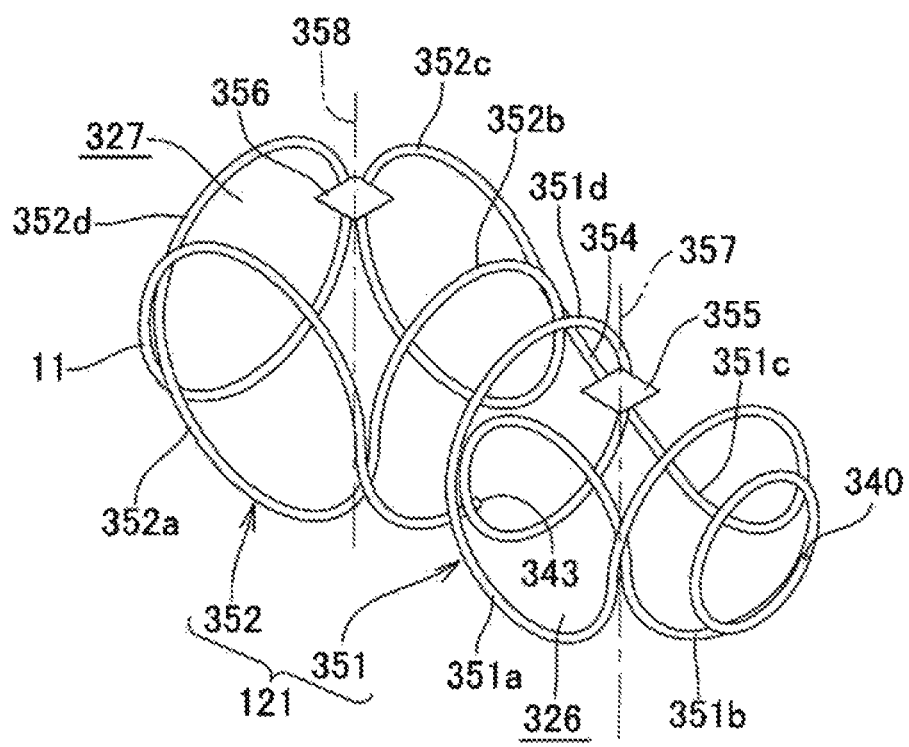

[Fig. 11]
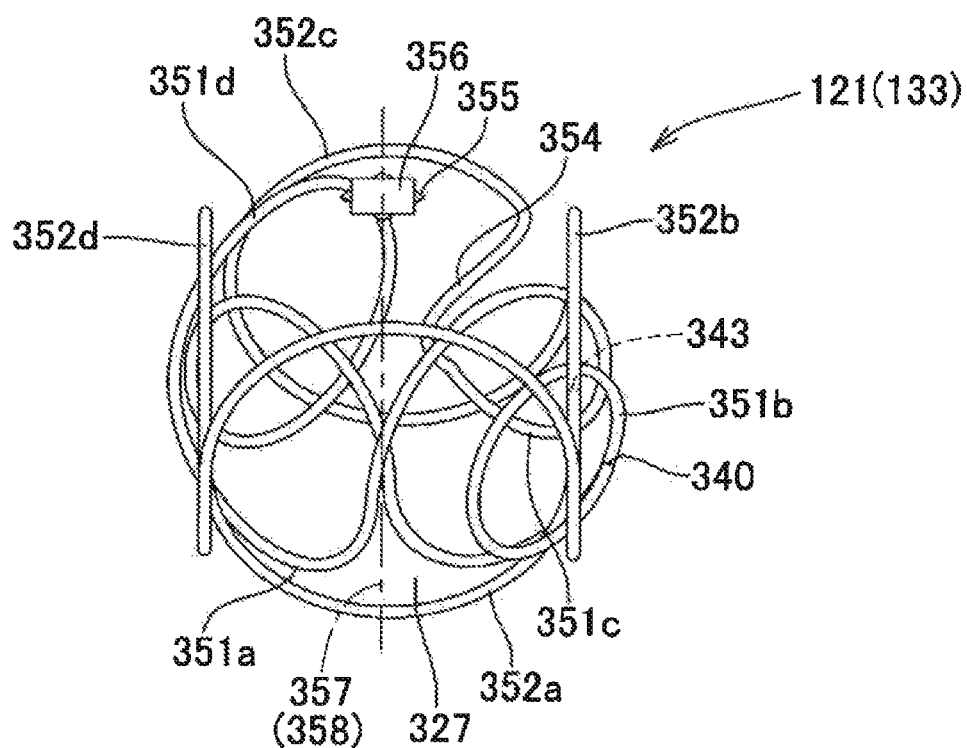
[Fig. 12]
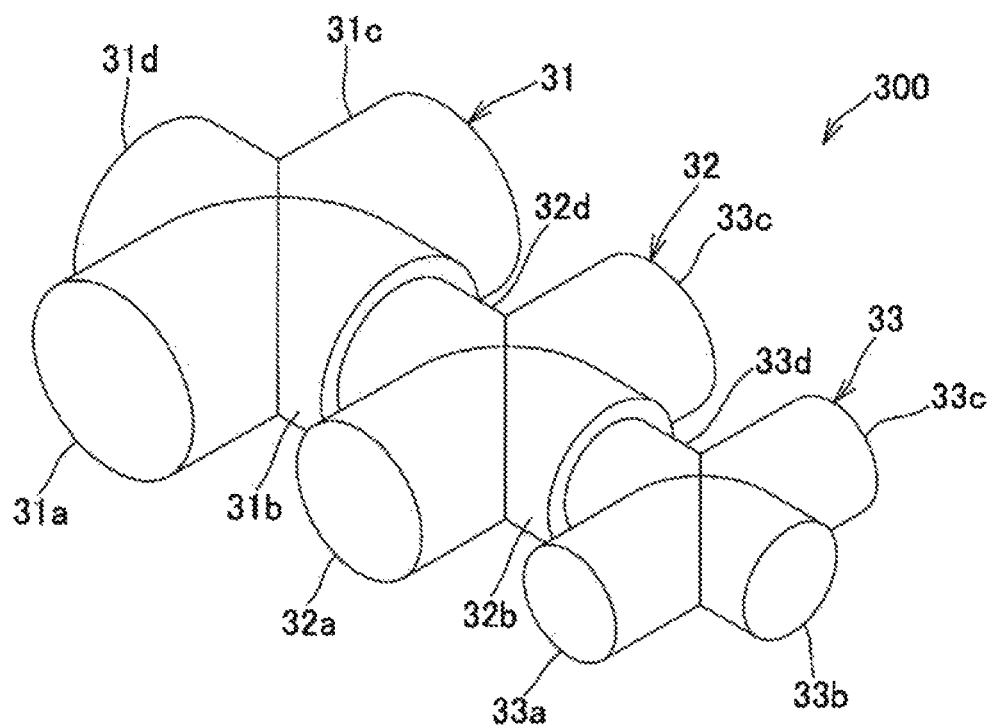

[Fig. 13]
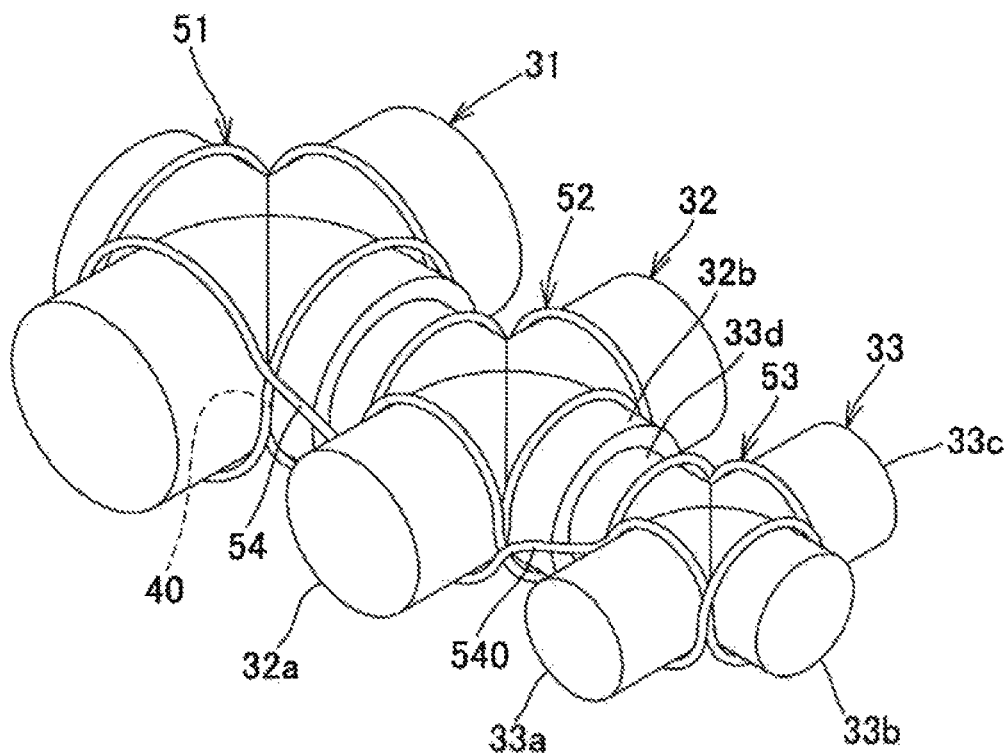
[Fig. 14]
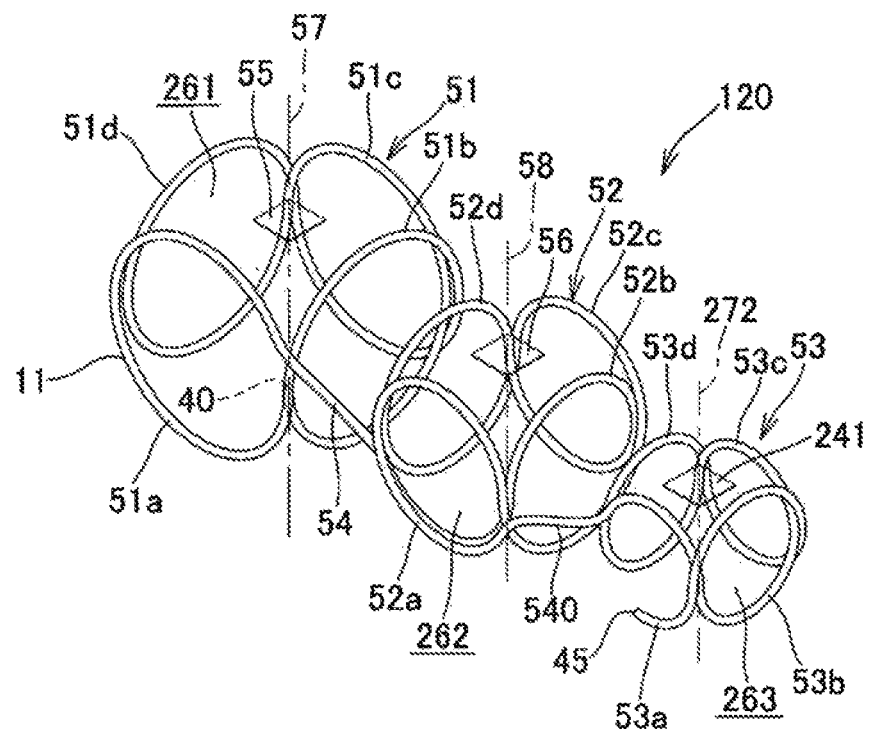

[Fig. 15]
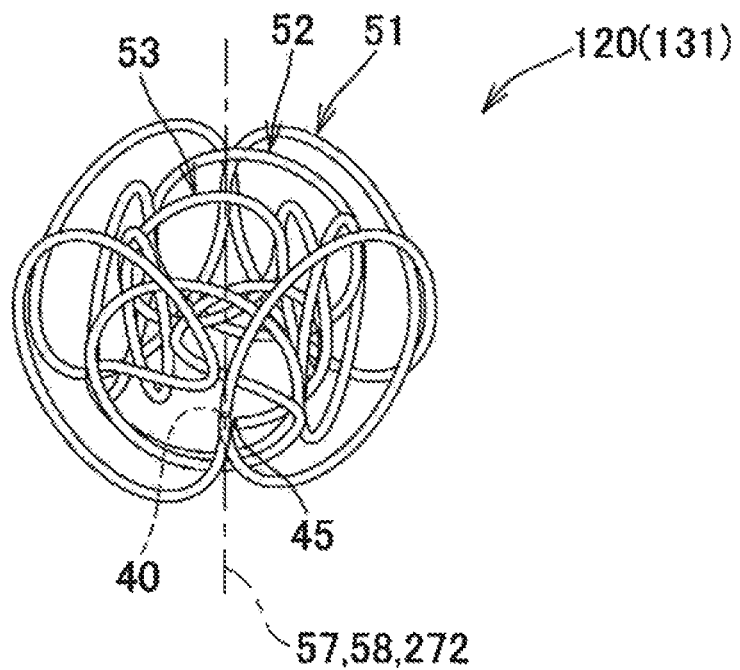
[Fig. 16]
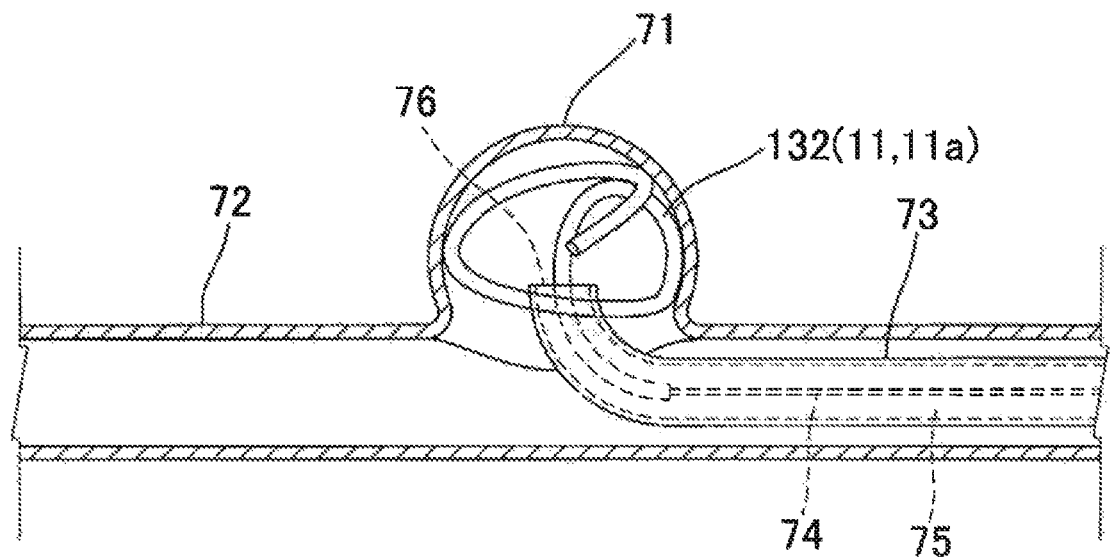

US 10,709,453 B2

IN VIVO INDWELLING MEMBER AND METHOD FOR PRODUCING SAME

TECHNICAL FIELD

The present invention relates to an in vivo indwelling member and a method for producing the same, and, for example, to an in vivo indwelling member that includes a secondary coil and a method for producing the same.

BACKGROUND ART

In order to treat an aneurysm generated in a blood vessel or the like, a method by which to embed a metallic coil in the aneurysm to embolize the aneurysm and prevent it from being ruptured is employed. Such a metallic coil used as an in vivo indwelling member is a secondary coil formed such that a wire of platinum or the like is shaped in a coiled form and extended in a linear manner to form a primary coil, and then the primary coil is further shaped in a coiled form and extended in a linear manner. The metallic coil in the state of the primary coil extended in a linear manner is inserted into the lumen of a delivery catheter and delivered to a desired site. When removed from the catheter, the metallic coil is restored to the state of the secondary coil.

To embolize the aneurysm, it is considered as advantageous in treatment to spread the metallic coil in various directions without confining at one site in the inside of the aneurysm. Accordingly, a secondary shape given to the metallic coil (the shape of the secondary coil) is desirably a three-dimensional shape likely to intricately spread, not a two-dimensional coiled shape extending linearly as described above. Therefore, there have been proposed secondary coils having such a three-dimensional shape.

For example, Patent Document 1 discloses a substantially spherical or elliptic spherical secondary coil and a method for producing the same. The secondary coil is formed by winding a primary coil around a substantially spherical or elliptic spherical core and thermally shaping the coil.

In addition, Patent Document 2 discloses a method for producing a spherical secondary coil. The secondary coil is formed by winding and shaping a coil around mandrel in which one or more metallic rods are radially erected on the surface of a spherical core. Patent Document 2 also discloses a method for providing a secondary shape by the use of a "candy mold"-type tool. According to this method, a spherical secondary coil is obtained by shaping a coil in a spherical lumen.

Further, Patent Document 3 discloses a method for producing a spherical secondary coil. The secondary coil is formed by fitting a primary coil into a groove in a spherical shaft that has in the surface the groove into which the primary coil is to be fit.

Moreover, Patent Document 4 discloses a secondary coil having a three-dimensional orthogonal shape and a method for producing the same. The secondary coil is formed by winding a coil around a mandrel with a three-dimensional orthogonal shape and thermally shaping the coil.

CITATION LIST

Patent Literature

Patent Document 1: Japanese Patent No. 3665133
Patent Document 2: Japanese Patent No. 3024071
Patent Document 3: Japanese Patent No. 4065665
Patent Document 4: JP-T No. 2004-500929

SUMMARY OF THE INVENTION

Technical Problem

However, when the surface of the core around which the primary coil is wound has a smooth curve as in an embodiment described in Patent Document 1, the primary coil slips on the outer surface at the time of winding and the shaping of the coil is difficult. In addition, when the spherical core has intricate grooves on the surface as in another embodiment described in Patent Document 1 and an embodiment described in Patent Document 3, it is not always easy to fit the primary coil in the intricate grooves on the surface of the sphere. It is also always not easy to provide grooves in the core of the same size as an aneurysm, that is, a diameter of about 1 to 30 mm. In particular, it is very difficult to form grooves in a core with a diameter of about 1 to 10 mm.

When it is possible to produce a mandrel with one or more metallic rods erected radially on the surface of a spherical core as in an embodiment described in Patent Document 2, it is regarded as relatively easy to wind and fix the primary coil around the curve surface of the core as compared to the case where the primary coil is fitted into the grooves in the core as described above. However, it is not always easy to arrange metallic rods on the spherical core of the same size as an aneurysm, that is, a diameter of about 1 to 30 mm. In particular, it is considered as very difficult to arrange metallic rods on a core with a diameter of about 1 to 10 mm.

According to the production method with the use of a "candy mold"-type tool described in Patent Document 2, primary coils are arranged at random in the lumen of the mold, and it is considered as very difficult to produce the coils of the same shape and conduct proper quality control.

According to the production method described in Patent Document 4, the single mandrel with a three-dimensional orthogonal shape is used, and it is easy to wind and fix the primary coil around the mandrel as compared to the methods described in Patent Documents 1 to 3, and it is possible to form the coils of the same shape. However, according to this production method, a simple cubic shape can be obtained but an intricately spreading three-dimensional secondary coil cannot be produced.

The present invention is devised to solve the foregoing problems. An object of the present invention is to provide an in vivo indwelling member having an intricately spreading three-dimensional secondary coil, and a method for producing the in vivo indwelling member in an easy and simple manner.

Solution to Problem

As a result of intensive studies to solve the above problems, the inventor of the present application has found out that the foregoing object could be attained by the following configuration. An outline of the present invention is as follows:

A first aspect of the present invention relates to a method for producing an in vivo indwelling member having a secondary coil in which a secondary shape is given to a linear primary coil with a primary shape given to a linear material, the method including: a first three-dimensional body formation step of forming a first three-dimensional body by aligning in a loop a plurality of segments, each of the segments being formed by winding the primary coil at least once, so that a part of the primary coil is spatially arranged; a second three-dimensional body formation step of forming a second three-dimensional body by aligning in a loop a plurality of segments, each of the segments being formed by winding the primary coil at least once, so that at least a part of the rest of the primary coil is spatially arranged after the formation of the first three-dimensional body; and an inside arrangement step of arranging one of the first and second three-dimensional bodies inside a loop part formed of the plurality of segments aligned in a loop of the other three-dimensional body.

A second aspect of the present invention relates to a method for producing an in vivo indwelling member having a secondary coil in which a secondary shape is given to a linear primary coil with a primary shape given to a linear material, the method including: a first three-dimensional body formation step of forming a first three-dimensional body by aligning in a loop a plurality of segments, each of the segments being formed by winding the primary coil at least once, so that a part of the primary coil is spatially arranged; a second three-dimensional body formation step of forming a second three-dimensional body by aligning in a loop a plurality of segments, each of the segments being formed by winding the primary coil at least once, so that at least a part of the rest of the primary coil is spatially arranged after the formation of the first three-dimensional body; an additional three-dimensional body formation step of forming an additional three-dimensional body by aligning in a loop a plurality of segments, each of the segments being formed by winding the primary coil at least once, so that at least a part of the rest of the primary coil is spatially arranged after the formation of the first and second three-dimensional bodies; a first inside arrangement step of arranging one of the first, second and additional three-dimensional bodies inside a loop part formed of the plurality of segments aligned in a loop of one of the two remaining three-dimensional bodies; and a second inside arrangement step of arranging the one remaining three-dimensional body inside the loop part formed of the plurality of segments aligned in a loop of the three-dimensional body, which is arranged inside at the first inside arrangement step, or arranging the two three-dimensional bodies after the first inside arrangement step inside the loop part formed of the plurality of segments aligned in a loop of the one remaining three-dimensional body.

According to the production method of the present invention, it is desired that one three-dimensional is smaller than another three-dimensional body and is arranged inside the loop part of the another three-dimensional body.

According to the production method of the present invention, it is desired that the three-dimensional bodies are formed in polygonal cylindrical shapes, in which the pluralities of segments are aligned in loops, and the shapes of the polygons are the same and the size of the polygons are the same or different among the three-dimensional bodies with regard to the shapes recognized in a cross-sectional direction orthogonal to central axes of the cylindrical three-dimensional bodies.

According to the production method of the present invention, the three-dimensional bodies each formed in a polygonal cylindrical shape may be arranged such that the central axes of the adjacent three-dimensional bodies are in a positional relationship of crossing or of a skew position.

According to the production method of the present invention, the three-dimensional bodies formed in polygonal cylinders may be arranged such that the central axes are concentric or parallel and the sides of the polygons of the adjacent three-dimensional bodies are not parallel.

Moreover, according to the production method of the present invention, the shape of the segments is desirably at least one kind selected from among polygon, broken line, arc, circle, elliptic arc, ellipse, and spiral.

In addition, according to the production method of the present invention, the primary coil constituting the segments is preferably arranged two-dimensionally or three-dimensionally.

In addition, according to the production method of the present invention, the segments are preferably formed by winding the primary coil around a mandrel at least once. In this case, the mandrel is preferably structured to have at least two connected parts with annular arrangement of rod-shaped portions around which the primary coil can be wound.

A third aspect of the present invention relates to an in vivo indwelling member having a secondary coil in which a secondary shape is given to a linear primary coil with a primary shape given to a linear material, the member including: a first three-dimensional body in which a plurality of segments, each of the segments being formed by winding a part of the primary coil at least once, is aligned in a loop and the part of the primary coil is spatially arranged; and a second three-dimensional body in which a plurality of segments, each of the segments being formed by winding at least a part of the rest of the primary coil after the formation of the first three-dimensional body at least once, is aligned in a loop and at least the part of the rest of the primary coil is spatially arranged, in which one of the first and second three-dimensional bodies is arranged inside a loop part formed of the plurality of segments aligned in a loop of the other three-dimensional body.

The in vivo indwelling member according to the present invention may further include an additional three-dimensional body in which a plurality of segments, each of the segments being formed by winding at least a part of the rest of the primary coil after the formation of the first and second three-dimensional bodies at least once, is aligned in a loop and at least the part of the rest of the primary coil is spatially arranged, wherein one of the first and second three-dimensional bodies and the additional three-dimensional body is arranged inside the loop part formed by aligning the plurality of segments of one of the two remaining three-dimensional bodies, and the other of the two remaining three-dimensional bodies is arranged inside the loop part of the one of the two remaining three-dimensional bodies.

In the in vivo indwelling member according to the present invention, it is desired that one three-dimensional body is smaller than another three-dimensional body and is arranged inside the loop part of the another three-dimensional body.

In the in vivo indwelling member according to the present invention, it is desired that the three-dimensional bodies are formed in polygonal cylindrical shapes, in which the pluralities of segments are aligned in loops, and the shapes of the polygons are the same and the size of the polygons are the same or different among the three-dimensional bodies with regard to the shapes recognized in a cross-sectional direction orthogonal to central axes of the cylindrical three-dimensional bodies.

In the in vivo indwelling member according to the present invention, the central axes of the adjacent three-dimensional bodies may be in a positional relationship of crossing or of a skew position.

In the in vivo indwelling member according to the present invention, the three-dimensional bodies each formed in a polygonal cylindrical shape may be arranged such that the central axes are concentric or parallel and the sides of the polygons of the adjacent three-dimensional bodies are not parallel.

In the in vivo indwelling member according to the present invention, the shape of the segments is desirably at least one kind selected from among polygon, broken line, arc, circle, elliptic arc, ellipse, and spiral.

The primary coil constituting the segments is preferably arranged two-dimensionally or three-dimensionally.

Advantageous Effects of Invention

According to the present invention, it is possible to provide an in vivo indwelling member having an intricately spreading three-dimensional secondary coil and a method for producing the in vivo indwelling member in an easy and simple manner.

BRIEF DESCRIPTION OF THE DRAWINGS

FIG. 1A is a plane view of a wire;
FIG. 1B is a plane view of a mandrel for providing a primary shape;
FIG. 1C is a plane view illustrating a mode of a primary coil;
FIG. 1D is a plane view of a primary coil in another mode;
FIG. 2A is a schematic perspective view of a three-dimensional body in which four circular segments are aligned in a loop and arranged in a spatial manner as a model;
FIG. 2B is a schematic perspective view of three-dimensional arrangement of the segments in the three-dimensional body illustrated in FIG. 2A as a virtual model of a cubic body;
FIG. 2C is a front view of the three-dimensional body illustrated in FIG. 2A or the cubic body illustrated in FIG. 2B as seen from a direction of a central axis;
FIG. 3 is a schematic perspective view of an example of a mandrel usable in a method for producing an in vivo indwelling member according to the present invention;
FIG. 4 is a schematic perspective view of an initial state in a first three-dimensional body formation step in an example of method for producing an in vivo indwelling member according to the present invention;
FIG. 5 is a schematic perspective view of a state after the first three-dimensional body formation step in the example of method for producing an in vivo indwelling member according to the present invention;
FIG. 6 is a schematic perspective view of a state after a second three-dimensional body formation step in the example of method for producing an in vivo indwelling member according to the present invention;
FIG. 7A is a perspective view of an initial arrangement state of a first three-dimensional body and a second three-dimensional body at an inside arrangement step in the example of method for producing an in vivo indwelling member according to the present invention;
FIG. 7B is a perspective view of an intermediate state in which the second three-dimensional body is arranged inside a loop part of the first three-dimensional body at the inside arrangement step in the example of method for producing an in vivo indwelling member according to the present invention;
FIG. 7C is a perspective view of an intermediate state in which the second three-dimensional body is arranged inside a loop part of the first three-dimensional body after the state illustrated in FIG. 7B at the inside arrangement step in the example of method for producing an in vivo indwelling member according to the present invention;
FIG. 7D is a schematic perspective view of a state in which the second three-dimensional body is arranged in the loop part of the first three-dimensional body or shape and structure of a finally obtained secondary coil at the inside arrangement step in the example of method for producing an in vivo indwelling member according to the present invention;
FIG. 7E is an illustrative diagram for describing positional relationship between the first three-dimensional body and the second three-dimensional body illustrated in FIG. 7D;
FIG. 8A is a perspective view of another state in which the second three-dimensional body is arranged inside the loop part of the first three-dimensional body at the inside arrangement step in the example of method for producing an in vivo indwelling member according to the present invention;
FIG. 8B is an illustrative diagram for describing positional relationship between the first three-dimensional body and the second three-dimensional body illustrated in FIG. 8A;
FIG. 9 is a schematic perspective view of a state after the second three-dimensional body formation step with the use of another example of a mandrel in the example of method for producing an in vivo indwelling member according to the present invention;
FIG. 10 is a perspective view illustrating an initial arrangement state of the first three-dimensional body and the second three-dimensional body at the inside arrangement step after the second three-dimensional body formation step with the use of another example of a mandrel illustrated in FIG. 9;
FIG. 11 is a schematic perspective view of a state in which the second three-dimensional body is arranged inside the loop part of the first three-dimensional body or shape and structure of the finally obtained secondary coil at the inside arrangement step after the second three-dimensional body formation step with the use of another example of a mandrel illustrated in FIG. 9;
FIG. 12 is a schematic perspective view of another example of a mandrel usable in the example of method for producing an in vivo indwelling member according to the present invention;
FIG. 13 is a schematic perspective view of a state after an additional three-dimensional body formation step in the example of method for producing an in vivo indwelling member according to the present invention;
FIG. 14 is a perspective view of an initial arrangement state of the first three-dimensional body, the second three-dimensional body, and an additional three-dimensional body at a first inside arrangement step in the example of method for producing an in vivo indwelling member according to the present invention;
FIG. 15 is a schematic perspective view illustrating an arrangement state of the first three-dimensional body, the second three-dimensional body, and the additional three-dimensional body or shape and structure of the finally obtained secondary coil after a second inside arrangement step in the example of method for producing an in vivo indwelling member according to the present invention; and
FIG. 16 is a schematic cross-sectional view of a state in which an in vivo indwelling member is inserting into an aneurysm.

DESCRIPTION OF EMBODIMENTS

Embodiments of the present invention will be described below with reference to the drawings. For the sake of convenience, some reference signs may be omitted in some drawings. In such a case, other drawings are to be referred to. In addition, for the sake of convenience, the dimensions of various members illustrated in the drawings may be adjusted for higher visibility.

In the present invention, a primary shape means a shape firstly given to a linear material. For example, the primary shape is a spiral shape as illustrated in FIGS. 1C and 1D firstly given to a wire 10 as a single linear material as illustrated in FIG. 1A by winding around a mandrel 14 or the like as a linear rod-shaped member as illustrated in FIG. 1B. The wire 10 given the primary shape as a spiral shape illustrated in FIG. 1C or 1D will be called primary coil 11 or 11a, for example.

An intermediate shape described later means a shape given to the primary coil through a first three-dimensional body formation step and a second three-dimensional body formation step, and as necessary an additional three-dimensional body formation step. For example, the primary coils 11 and 11a are shaped to have a first three-dimensional body 51 and a second three-dimensional body 52 illustrated in FIG. 7A, or the first three-dimensional body 51, the second three-dimensional body 52, and an additional three-dimensional body 53 illustrated in FIG. 14, each of the three-dimensional bodies being arranged outside another three-dimensional body. For example, the primary coils 11 and 11a given the intermediate shapes illustrated in FIGS. 7A and 14 will be called intermediate-shape coils (12 and 120).

In the present invention, a secondary shape means a shape given to the primary coil having the shape given through the first three-dimensional body formation step and the second three-dimensional body formation step or through the two formation steps and the additional three-dimensional body formation step as necessary, through an inside arrangement step or first and second inside arrangement steps. For example, the secondary shape means a final shape given to the intermediate-shape coil (12 or 120) illustrated in FIG. 7A or 14 in such a manner as illustrated in FIG. 7D or 15, respectively. For example, the primary coil (11 or 11a) in which the secondary shape illustrated in FIG. 7D, 8A, or 15 is fixed and given to the intermediate-shape coil (12 or 120) will be called secondary coil (13, 130, or 131).

At the formation of the first three-dimensional body, the second three-dimensional body, and the additional three-dimensional body, aligning a plurality of segments in a loop and spatially arranging the primary coil means arranging the primary coil in a three-dimensional shape other than a coiled and linearly extending shape (for example, coil shapes formed by winding the primary coil as illustrated in FIGS. 1C and 1D).

Arranging two-dimensionally the primary coil constituting segments means that the primary coil in one segment exists in the same plane. In this case, the primary coil may exist in exactly the same plane or in planes regarded as substantially the same.

Arranging three-dimensionally the primary coil constituting segments means that the primary coil in one segment is arranged not in the same plane but the one entire segment forms a three-dimensional structure. One segment may be structured to extend in a coiled linear manner or may be structured in a three-dimensional arrangement.

The shape recognized in the cross sectional direction orthogonal to the central axis of a cylindrical three-dimensional body means not only the shape of the cross section of the primary coil but also the shape recognized from the segments formed by winding the primary coil.

The state in which a three-dimensional body is arranged inside the loop part of the plurality of segments aligned in a loop of another three-dimensional body means the state resulting from arrangement of a three-dimensional body inside the loop part of another three-dimensional body. This state means not only that the primary coil constituting the three-dimensional body arranged inside does not protrude from the loop part but also that the primary coil protrudes as far as it does not inhibit the function of the in vivo indwelling member.

First Embodiment

The linear primary coil formed by giving the primary shape to a linear material for use in the present invention will be described.

First, the primary coil for use in the present invention is formed by giving the primary shape to a wire 10 as a linear material as illustrated in FIG. 1A, for example. The wire 10 is a linear member (linear material). There is no particular limitation on the structure of the linear material as far as the linear material can be spirally wound to form a coil shape. The linear material may be a single wire or a stranded wire formed by stranding a plurality of single wires. In addition, the linear material is formed in a linear fashion as a whole, and the shape of the cross section orthogonal to the longitudinal side can be selected as appropriate from among a circle, an ellipse, a polygon such as a rectangle, and the like. In the case of using the stranded wire, the entire stranded wire has such a shape. The wire 10 illustrated in FIG. 1A is a single wire having a circular cross section and extending in a linear fashion although not depicted.

There is no particular limitation on the material for the linear material, and the material may be platinum, tungsten, gold, stainless steel, or an alloy of tungsten and platinum, for example. These materials are radiopaque materials. In addition, the width and diameter of the linear material can be selected as appropriate depending on the purpose of use or the like without particular limitation. For example, in the case of using the linear material for treatment of aneurysm obliteration, the width or the diameter is preferably 0.010 to 0.200 mm, more preferably 0.030 to 0.100 mm.

The linear material such as the wire 10 described above is given the primary shape to form the primary coil. The primary coil is formed by winding the wire 10 around a mandrel 14 illustrated in FIG. 1B, for example. The shape and structure of the mandrel can be selected as appropriate according to the desired shape of the primary coil as far as the linear material can be wound around the mandrel. For example, in the example illustrated in FIG. 1B, the mandrel is a columnar or circular cylindrical linear rod-shaped member that is substantially constant in outer diameter in the longitudinal direction. Besides, the mandrel may be changed in outer diameter in the longitudinal direction, or may be prismatic in shape, or may be square tubular in shape with a polygonal cross section, or the like. By selecting as appropriate the shape of the mandrel and the manner of winding the linear material around the mandrel, it is possible to obtain a primary coil 11 or 11a in which the wire 10 is spirally wound and the coiled primary shape with a constant outer diameter is given as illustrated in FIG. 1C or 1D, for example. The shape of the primary coil is preferably linear. The linear shape here means that the linear material has a structure in which the spiral part of the linear material extends continuously in a linear fashion. For example, the overall linear structure as illustrated in FIG. 1C or 1D may be used. The outer diameter or width of the primary coil 11 or 11a as illustrated in FIG. 1C or 1D can be selected as appropriate depending on the purpose of use or the like without particular limitation. For example, in the case of using the primary coil for treatment of aneurysm obliteration, the outer diameter or width is preferably 0.100 to 0.500 mm. In addition, the entire length of the primary coil 11 can also be selected as appropriate depending on the purpose of use without particular limitation. For example, in the case of using the primary coil for treatment of aneurysm obliteration, the entire length is preferably 10 to 1000 mm.

There is no particular limitation on the pitch of the primary coil. For example, the adjacent portions of the wire 10 may closely attach to each other as illustrated in FIG. 1C, or the adjacent portions of the wire 10 may be separated from each other as illustrated in FIG. 1D. The adjacent portions of the wire may closely attach to each other over the entire length of the primary coil 11 in the longitudinal direction, or the adjacent portions of the wire may be separated from each other over the entire length of the primary coil 11 in the longitudinal direction, or the wire may have one or more tight-pitch portions and one or more larger-pitch portions in the longitudinal direction of the primary coil.

The in vivo indwelling member of the present invention has: a first three-dimensional body in which a plurality of segments generated by winding part of the primary coil at least once is aligned in a loop, and part of the primary coil is spatially arranged; and a second three-dimensional body in which a plurality of segments generated by winding at least once at least part of the rest of the primary coil with the first three-dimensional body is aligned in a loop, and at least part of the rest of the primary coil is spatially arranged.

The first three-dimensional body and the second three-dimensional body are common in the structure in which a plurality of segments generated by winding part of the primary coil at least once is aligned in a loop and part of the primary coil is spatially arranged. Accordingly, the structural features will be collectively described below.

An embodiment of a three-dimensional body in which a plurality of segments is aligned in a loop and spatially arranged will be described with reference to the model illustrated in FIGS. 2A to 2C. FIG. 2A is a perspective view of a three-dimensional body 20 in which four circular segments (21a, 21b, 21c, and 21d) are aligned in a loop and spatially arranged as a model. FIG. 2B is a diagram for describing the spatial arrangement of the segments of the three-dimensional body 20 illustrated in FIG. 2A as a model of a cubic body. FIGS. 2A to 2C illustrate the segments by lines for describing the models. The segments correspond to segments formed by winding part of the primary coil at least once described above.

The four segments (21a, 21b, 21c, and 21d) of the three-dimensional body 20 illustrated in FIG. 2A are arranged in a loop to form four side surfaces (23a, 23b, 23c, and 23d) of a cubic body 22 as a model as illustrated in FIG. 2B.

In the example illustrated in FIGS. 2A and 2B, the segments (21a, 21b, 21c, and 21d) are arranged to form the four side surfaces of the cubic body 22, thereby constituting a loop part 21. The loop part 21 is a one-winding loop part formed by the segments aligned in a linear fashion (in series). Meanwhile, an upper surface 24 and a lower surface 25 of the cubic body 22 exist in the model, but no segment is arranged at parts of the three-dimensional body 20 corresponding to the upper surface 24 and the lower surface 25 of the cubic body 22. In the present invention, the parts without segment will be called openings. The openings are different from a spatial part surrounded by the circular primary coil in the segment 21a illustrated in FIG. 2A, for example.

The loop part has a central axis in a direction orthogonal to the direction in which the segments are aligned in a loop (a plane generated by arranging the segments in a loop). In the example of FIGS. 2A and 2B, a central axis 27 of the loop part 21 is formed in the direction in which the segments (21a, 21b, 21c, and 21d) are aligned, that is, in the direction orthogonal to the direction in which the side surfaces (23a, 23b, 23c, and 23d) of the cubic body 22 are aligned. In this case, the direction orthogonal to the direction in which the segments are aligned in a loop may not necessarily be the strictly orthogonal direction.

As described above, the three-dimensional body 20 illustrated in FIG. 2A has the cylindrical loop part 21 formed by arranging the segments in a loop, and a hollow portion 26 opening at the both ends of the loop part 21 in the direction of the central axis 27 inside the loop part 21. In addition, as described later, another three-dimensional body can be arranged in the hollow portion 26 from the openings.

When the three-dimensional body 20 or the cubic body 22 illustrated in FIG. 2A or 2B from the direction of the central axis 27 of the three-dimensional body 20, that is, from the side of the upper surface 24 or the lower surface 25 of the cubic body 22, a loop regular square formed from the four segments (21a, 21b, 21c, and 21d) or the four side surfaces (23a, 23b, 23c, and 23d) is recognized as illustrated in FIG. 2C (in a front view from the upper surface 24 side). That is, in the three-dimensional body 20, the loop part 21 formed from the segments (21a, 21b, 21c, and 21d) has a regular square cylindrical shape. In this case, the loop part 21 has also a regular square shape recognized from the cross-sectional direction orthogonal to the central axis 27. The shape recognized in the cross-sectional direction orthogonal to the central axis does not mean the shape recognized only from the primary coil constituting the segments but means the shape recognized when the shape recognized from the entire loop part 21 including the primary coil is assumed. For example, the foregoing shape means the entire shape of the side surfaces (23a, 23b, 23c, and 23d) of the cubic body 22 illustrated in FIG. 2B.

In the following description, an upper opening surface 24a and a lower opening surface 25a corresponding to the upper surface 24 and the lower surface 25 illustrated in FIG. 2B may be assumed at the two openings in the three-dimensional body 20 as illustrated in FIG. 2A. The opening surfaces 24a and 25a are orthogonal to the central axis 27.

In the example of FIG. 2A, all the segments (21a, 21b, 21c, and 21d) are circular in shape. However, the shape of the segments is not limited to this but may be circle, arc, ellipse, elliptic arc, polygon, broken line, spiral, or the like, for example. Preferably, at least one is selected from among circle, arc, ellipse, elliptic arc, scroll, and spiral close to the shape of inner wall surface of an aneurysm. The segments are the same or different in shape. Even when the segments have an arc shape or the like and do not form a closed plane, for example, the foregoing description is applied assuming virtual planes in which the arcs or the like exist. In addition, all the segments (21a, 21b, 21c, and 21d) illustrated in FIG. 2A are the same in size. However, the embodiment is not limited to this but the segments may be different in size. Further, there is no particular limitation on the number of the segments as far as the segments can be aligned in a loop, although the number of the segments is four in FIG. 2A. However, the number of the segments is preferably three to six from the viewpoint of ease of manufacturing a mandrel 30 described later. The shape recognized in the cross-sectional direction orthogonal to the central axis of the loop part can be a polygon according to the number of the segments. For example, when the number of the segments is three, the shape recognized in the cross-sectional direction orthogonal to the central axis of the loop part is a triangle. The polygon may be or may not be a regular polygon.

In the example of FIG. 2A, the primary coil constituting the segments is arranged two-dimensionally, that is, on the same plane. Alternatively, the primary coil may be arranged three-dimensionally. The shape of the three-dimensional arrangement may be a spiral or the like. The spiral shape may be formed by winding the primary coil less than once, or once, or more than once. The diameter or width of winding in a two-dimensional plane or the spacing in (the pitch of) the primary coil in the three-dimensional direction may be constant or varied. In this case as well, the segments are preferably formed by arranging continuously and three-dimensionally the primary coil of the foregoing shape, that is, circle, arc, ellipse, elliptic arc, polygon, broken line, scroll, spiral, or the like.

The segments may be all formed by two-dimensional arrangement of the primary coil, or three-dimensional arrangement of the primary coil, or a combination of two-dimensional arrangement and three-dimensional arrangement of the primary coil.

FIGS. 2A to 2C illustrate the case in which the segments are formed by two-dimensional arrangement of the primary coil as an example. However, almost the same thing is applicable to the three-dimensional arrangement. For example, the same case as that in FIGS. 2A to 2C is applicable with reference to virtual planes as a model at the part facing the inside of the loop part of the plurality of segments aligned in a loop.

In the case of FIG. 2A, the arrangement of the segments (21a, 21b, 21c, and 21d) constituting the three-dimensional body 20, in other words, the overall structure of the loop part 21 is a regular square cylinder formed by the side surfaces of the cubic body 22 illustrated in FIG. 2B. However, the present invention is not limited to this but the structure is a polyhedral cylinder, a circular cylinder, or an elliptic cylinder, for example. More specifically, the polyhedral cylinder may be a cylinder with a polygonal cross section of a size constant or varying in the direction of the central axis, a cylinder with a regular polygonal cross section, a regular polyhedral cylinder with a larger number of planes than a regular octahedron, or the like. The cylinder may be a straight-tube cylinder, a frustoconical cylinder, a barrel-shaped cylinder, or the like.

In the present invention, the loop part is preferably formed from the segments such that the one primary coil described above is used unicursally while suppressing overlaps in the longitudinal direction of the primary coil. Accordingly, as described later, one of the first and second three-dimensional bodies can be easily inserted into the inside of the loop part of the other three-dimensional body. In addition, when inserted into an aneurysm, the primary coil can form a three-dimensional body extending evenly and intricately. Further, there is no need to use a mandrel having a conventional complicated groove structure.

In the present invention, as described above, in the first three-dimensional body and the second three-dimensional body, the plurality of segments generated by winding part of the primary coil at least once is aligned in a loop and part of the primary coil is spatially arranged. In addition, as described above, one of the first three-dimensional body and the second three-dimensional body having a spatial structure as illustrated in FIGS. 2A to 2C is arranged in the hollow portion 26 inside the loop part 21 of the other three-dimensional body. The details will be provided later.

An embodiment of an in vivo indwelling member and a method for producing the same according to the present invention will be described with reference to FIGS. 3 to 11. FIGS. 3 to 8B represent the coil shape of the linear material by flat planes, in the linear primary coil formed by shaping the linear material in a coiled form for simplified illustration.

In the present invention, first, the primary coil as described above is used to form the first three-dimensional body by aligning in a loop a plurality of segments formed by winding the primary coil at least once and spatially arranging part of the primary coil (a first three-dimensional body formation step). Then, the second three-dimensional body is formed by spatially arranging at least part of the rest of the primary coil with the first three-dimensional body (a second three-dimensional body formation step).

In the present invention, these steps are preferably carried out by winding the primary coil around a mandrel, for example. In addition, the segments are more preferably formed by winding the primary coil at least once around the mandrel.

FIG. 3 is a schematic perspective view of an example of mandrel usable in this example. The mandrel 30 illustrated in FIG. 3 has a first three-dimensional body formation part 31 that forms a first three-dimensional body 51 (see FIG. 6) and a second three-dimensional body formation part 32 that forms a second three-dimensional body 52 (see FIG. 6), and these parts are connected together. The first three-dimensional body formation part 31 has four first rod-shaped portions (31a, 31b, 31c, and 31d). The first rod-shaped portions (31a, 31b, 31c, and 31d) are annularly arranged such that their axes face in a radial direction and are integrated at a crossover site. The second three-dimensional body formation part 32 has four second rod-shaped portions (32a, 32b, 32c, and 32d). The second rod-shaped portions (32a, 32b, 32c, and 32d) are arranged annularly such that axes of the second rod-shaped portions face in a radial direction and are integrated at a crossover site. In this example, the one first rod-shaped portion 31b of the four first rod-shaped portions in the first three-dimensional body formation part 31 and the one second rod-shaped portion 32d of the four second rod-shaped portions in the second three-dimensional body formation part 32 are coupled together. In addition, the two parts are connected such that a central axis of the first rod-shaped portions 31b and 31d and a central axis of the second rod-shaped portions 32b and 32d are aligned with each other in the axial direction. The first three-dimensional body formation part 31 and the second three-dimensional body formation part 32 are examples for the formation of the structure of the three-dimensional body 20 illustrated in FIG. 2A as described above. The first rod-shaped portions (31a, 31b, 31c, and 31d) and the second rod-shaped portions (32a, 32b, 32c, and 32d) are orthogonal to each other in a cross shape and are all circular in cross section.

The structures of the first three-dimensional body formation part and the second three-dimensional body formation part can be selected as appropriate depending on the desired shapes of the first and second three-dimensional bodies. The shapes of the three-dimensional bodies are as described above. The widths or outer diameters of the first rod-shaped portions (31a, 31b, 31c, and 31d) and the second rod-shaped portions (32a, 32b, 32c, and 32d) in the direction orthogonal to the axial direction can be selected as appropriate depending on the purpose of use of the in vivo indwelling member, the shapes and structures of the first three-dimensional body and the second three-dimensional body. For example, in the case of using the in vivo indwelling member for treatment of aneurysm obliteration, the widths or diameters are preferably 1 to 30 mm. This is because the diameters of the rod-shaped portions of the mandrel 30 determine the size of a loop of one segment in the secondary coil and the diameter of the loop is preferably similar to the diameter of an aneurysm (1 to 30 mm).

The sizes, that is, the widths or outer diameters of the rod-shaped portions and the size of the crossover site of the rod-shaped portions of the first three-dimensional body formation part and the second three-dimensional body formation part are preferably different because one of the first and second three-dimensional bodies is easy to arrange inside the loop part of the other three-dimensional body as described later.

In addition, the first three-dimensional body formation part and the second three-dimensional body formation part are preferably structured such that, when the first three-dimensional body and the second three-dimensional body are formed in polygonal cylinders by these formation parts, the shapes of the polygons recognized in the cross-sectional directions orthogonal to the central axes of the two bodies are in a similarity relationship because the structures can be stably maintained after the inside arrangement step described later.

In the example of the mandrel 30 illustrated in FIG. 3, the four first rod-shaped portions (31a, 31b, 31c, and 31d) of the first three-dimensional body formation part 31 are equal in outer diameter, and the four second rod-shaped portions (32a, 32b, 32c, and 32d) of the second three-dimensional body formation part 32 are equal in outer diameter. However, the outer diameter of the first rod-shaped portions (31a, 31b, 31c, and 31d) is larger than the outer diameter of the second rod-shaped portions (32a, 32b, 32c, and 32d). Accordingly, the first three-dimensional body formation part 31 is larger than the second three-dimensional body formation part 32. Therefore, as for the sizes of the first three-dimensional body 51 and the second three-dimensional body 52 formed by the three-dimensional body formation parts, the first three-dimensional body 51 is larger than the second three-dimensional body 52. In addition, as for the shapes of the portions of the first three-dimensional body formation part 31 and the second three-dimensional body formation part 32 around which the primary coil 11 is wound, the polygons recognized in planes including the central axes of the first and second rod-shaped portions are regular squares in a similarity relationship. The first three-dimensional body 51 and the second three-dimensional body 52 formed by the formation parts are also in a similarity relationship.

Examples of the first three-dimensional body formation step and the second three-dimensional body formation step will be described taking the case in which the primary coil 11 illustrated in FIG. 1C is wound around the mandrel 30 illustrated in FIG. 3 as an example.

At the first three-dimensional body formation step, first, a core wire 38 longer than the entire primary coil 11 is preferably inserted into the lumen of the primary coil 11. Accordingly, the case of using the core wire will be described. After the insertion of the core wire, one end of the core wire 38 is preferably fixed to the mandrel 30 at a desired position from the viewpoint of workability. In the example of FIG. 4, the one end of the core wire 38 is fixed at a core wire fixation position with reference sign 39 on the peripheral surface of the first rod-shaped portion 31a of the mandrel 30 (the top in the arrangement of the first rod-shaped portion 31a illustrated in FIG. 4). There is no limitation on the fixation method, and the core wire 38 may be fixed by attaching a tape, or by using a fixation tool such as a clip or a screw provided in advance on the surface of the first rod-shaped portion 31a, or the like, as far as the fixation does not constitute an obstacle to winding of the primary coil 11. Next, the core wire 38 is wound around the first three-dimensional body formation part 31 of the mandrel 30 such that one end 40 of the primary coil 11 is located at a desired position on the first three-dimensional body formation part 31. In the example of FIG. 4, the one end 40 of the primary coil 11 is arranged at a winding start position with reference sign 35 on the peripheral surfaces of the first rod-shaped portions 31a and 31b (the position moved to the second three-dimensional body formation part 32 side about 90 degrees from the core wire fixation position with reference sign 39).

Then, the primary coil 11 is wound around the first rod-shaped portion (31a or 31b) closest to the winding start position 35 on the first three-dimensional body formation part 31. In this example, the primary coil 11 is wound along the peripheral surface of the first rod-shaped portion 31b illustrated at the lower side of FIG. 4. The primary coil 11 can be wound around the mandrel 30 by moving the mandrel 30 while applying tension by hanging a weight to the core wire 38 extending from the other end of the primary coil 11 not illustrated to the outside, for example.

At the first rod-shaped portion 31b illustrated at the lower side of FIG. 4, the primary coil 11 is wound about 180 degrees from the winding start position 35 in the direction orthogonal to the axial direction of the first rod-shaped portion 31b, and then the primary coil 11 reaches the connected site between the first rod-shaped portion 31b and the first rod-shaped portion 31c. Then, the direction of winding the primary coil 11 is changed, and the primary coil 11 is wound along the peripheral surface of the first rod-shaped portion 31c illustrated at the upper side of FIG. 4.

At the first rod-shaped portion 31c illustrated at the upper side of FIG. 4, the primary coil 11 is wound about 180 degrees from the connected site between the first rod-shaped portion 31b and the first rod-shaped portion 31c in the direction orthogonal to the axial direction of the first rod-shaped portion 31c, and then the primary coil 11 reaches the connected site between the first rod-shaped portion 31c and the first rod-shaped portion 31d. Then, the direction of winding the primary coil 11 is changed, and the primary coil 11 is wound along the peripheral surface of the first rod-shaped portion 31d illustrated at the lower side of FIG. 4, and then the primary coil 11 is wound along the peripheral surface of the first rod-shaped portion 31d illustrated at the upper side of FIG. 4. That is, the primary coil 11 is wound continuously in one turn around the first rod-shaped portion 31d in the direction orthogonal to the axial direction of the first rod-shaped portion 31d.

As described above, when the primary coil 11 is wound continuously in one turn around the first rod-shaped portion 31d, the primary coil 11 returns to the connected site between the first rod-shaped portion 31c and the first rod-shaped portion 31d. Then, the direction of winding the primary coil 11 is changed, and the primary coil 11 is wound along the peripheral surface of the first rod-shaped portion 31c illustrated at the lower side of FIG. 4.

At the first rod-shaped portion 31c illustrated at the lower side of FIG. 4, the primary coil 11 is wound about 180 degrees from the connected site between the first rod-shaped portion 31c and the first rod-shaped portion 31d in the direction orthogonal to the axial direction of the first rod-shaped portion 31c, and then the primary coil 11 returns to the connected site between the first rod-shaped portion 31b and the first rod-shaped portion 31c. Then, the direction of winding the primary coil 11 is changed, and the primary coil 11 is wound along the peripheral surface of the first rod-shaped portion 31b illustrated at the upper side of FIG. 4.

At the first rod-shaped portion 31b illustrated at the upper side of FIG. 4, the primary coil 11 is wound about 180 degrees from the connected site between the first rod-shaped portion 31b and the first rod-shaped portion 31c in the direction orthogonal to the axial direction of the first rod-shaped portion 31b, and then the primary coil 11 returns to the winding start position 35. Then, the direction of winding the primary coil 11 is changed, and the primary coil 11 is wound along the peripheral surface of the first rod-shaped portion 31a illustrated at the lower side of FIG. 4, and then the primary coil 11 is wound along the peripheral surface of the first rod-shaped portion 31a illustrated at the upper side of FIG. 4. That is, the primary coil 11 is wound continuously in one turn around the first rod-shaped portion 31a in the direction orthogonal to the axial direction of the first rod-shaped portion 31a. When the primary coil 11 is continuously wound in one turn around the first rod-shaped portion 31a, the primary coil 11 returns to the winding start position 35. In this way, the first three-dimensional body 51 is formed by the primary coil 11 wound around the first three-dimensional body formation part 31 and spatially arranged (in a cubic body in this example). FIG. 5 is a schematic perspective view of this state. Accordingly, the first three-dimensional body formation step is completed.

The primary coil is wound once around the first rod-shaped portions with reference signs 31a and 31d, and the primary coil is wound twice around the first rod-shaped portions with reference signs 31b and 31c as described above. The primary coil 11 arranged at the first rod-shaped portions forms the corresponding segments of the first three-dimensional body.

In this example, the primary coil 11 is unicursally wound around the first three-dimensional body formation part 31 as described above. In addition, the primary coil 11 is finally wound around the first rod-shaped portion 31a, out of the four first rod-shaped portions in the first three-dimensional body formation part 31, that is closer to the second three-dimensional body formation part 32 and has an axial direction orthogonal to the direction in which the first three-dimensional body formation part 31 and the second three-dimensional body formation part 32 align with each other. This suppresses displacement of the primary coil 11 at the switching site between the first three-dimensional body to be formed by the first three-dimensional body formation part 31 and the second three-dimensional body to be formed by the second three-dimensional body formation part 32 and its neighborhood, and facilitates the winding of the primary coil 11 around the mandrel 30 with the first three-dimensional body and the second three-dimensional body held in desired shapes.

After the primary coil 11 is wound around the first rod-shaped portion close to the winding start position 35, the primary coil 11 is further wound around the plurality of first rod-shaped portions. When the primary coil 11 reaches the connected site between the currently wound first rod-shaped portion and the adjacent first rod-shaped portion, the primary coil 11 is wound around the adjacent first rod-shaped portion or the current first rod-shaped portion depending on a choice made between: (i) changing the direction of winding to wind around the adjacent first rod-shaped portion; and (ii) winding continuously around the current first rod-shaped portion. Then, each time the primary coil reaches the connected site between the current first rod-shaped portion and the adjacent first rod-shaped portion, the foregoing choice is made to wind the primary coil 11 around the first three-dimensional body formation part 31 of the mandrel 30.

After the completion of the first three-dimensional body formation step, the second three-dimensional body formation step is performed to wind the rest of the primary coil 11 after the formation of the first three-dimensional body 51 around the second rod-shaped portions (32a, 32b, 32c, and 32d) of the second three-dimensional body formation part 32 to form the second three-dimensional body at the rest of the primary coil 11. FIG. 6 is a schematic perspective view of the state after the second three-dimensional body formation step.

At the second three-dimensional body formation step, first, the primary coil 11 is wound around the second rod-shaped portion 32a of the second three-dimensional body formation part 32 that has an axial direction parallel to the axial direction of the first rod-shaped portion 31a of the first three-dimensional body formation part 31 and is close to the winding start position 35 of the first three-dimensional body formation part 31. The primary coil 11 can be wound with tension applied to the core wire extending outward from the other end not illustrated of the primary coil 11 as at the first three-dimensional body formation step. In the example of FIG. 6, after winding along the peripheral surface of the first rod-shaped portion 31a of the first three-dimensional body formation part 31 illustrated at the upper side of FIGS. 4 and 6, the primary coil 11 is wound along the peripheral surface of the second rod-shaped portion 32a of the second three-dimensional body formation part 32 illustrated at the lower side of FIG. 6. Then, at the second rod-shaped portion 32a illustrated at the lower side of FIG. 6, the primary coil 11 is wound in the direction orthogonal to the axial direction of the second rod-shaped portion 32a, and then the primary coil 11 reaches the connected site between the second rod-shaped portion 32a and the second rod-shaped portion 32b. Then, the direction of winding the primary coil 11 is changed, and the primary coil 11 is wound along the peripheral surface of the second rod-shaped portion 32b illustrated at the upper side of FIG. 6.

At the second rod-shaped portion 32b illustrated at the upper side of FIG. 6, the primary coil 11 is wound about 180 degrees from the connected site between the second rod-shaped portion 32a and the second rod-shaped portion 32b in the direction orthogonal to the axis direction of the second rod-shaped portion 32b, and the primary coil 11 reaches the connected site between the second rod-shaped portion 32b and the second rod-shaped portion 32c. Then, the direction of winding the primary coil 11 is changed, and the primary coil 11 is wound along the peripheral surface of the second rod-shaped portion 32c illustrated at the lower side of FIG. 6.

At the second rod-shaped portion 32c illustrated at the lower side of FIG. 6, the primary coil 11 is wound about 180 degrees from the connected site between the second rod-shaped portion 32b and the second rod-shaped portion 32c in the direction orthogonal to the axial direction of the second rod-shaped portion 32c, and the primary coil 11 reaches the connected site between the second rod-shaped portion 32c and the second rod-shaped portion 32d. Then, the direction of winding the primary coil 11 is changed, and the primary coil 11 is wound along the peripheral surface of the second rod-shaped portion 32d illustrated at the upper side of FIG. 6, and then the primary coil 11 is continuously wound along the peripheral surface of the second rod-shaped portion 32d illustrated at the lower side of FIG. 6. That is, the primary coil 11 is continuously wound in one turn around the second rod-shaped portion 32d in the direction orthogonal to the axial direction of the second rod-shaped portion 32d.

When the primary coil 11 is continuously wound in one turn around the second rod-shaped portion 32d in this manner, the primary coil 11 returns to the connected site between the second rod-shaped portion 32c and the second rod-shaped portion 32d. Then, the direction of winding the primary coil 11 is changed, and the primary coil 11 is wound along the peripheral surface of the second rod-shaped portion 32c illustrated at the upper side of FIG. 6.

At the second rod-shaped portion 32c illustrated at the upper side of FIG. 6, the primary coil 11 is wound about 180 degrees from the connected site between the second rod-shaped portion 32c and the second rod-shaped portion 32d in the direction orthogonal to the axial direction of the second rod-shaped portion 32c, and the primary coil 11 returns to the connected site between the second rod-shaped portion 32b and the second rod-shaped portion 32c. Then, the direction of winding the primary coil 11 is changed, and the primary coil 11 is wound along the peripheral surface of the second rod-shaped portion 32b illustrated at the lower side of FIG. 6.

At the second rod-shaped portion 32b illustrated at the lower side of FIG. 6, the primary coil 11 is wound about 180 degrees from the connected site between the second rod-shaped portion 32b and the second rod-shaped portion 32c in the direction orthogonal to the axial direction of the second rod-shaped portion 32b, and the primary coil 11 returns to the connected site between the second rod-shaped portion 32a and the second rod-shaped portion 32b. Then, the direction of winding the primary coil 11 is changed, and the primary coil 11 is wound along the peripheral surface of the second rod-shaped portion 32a illustrated at the upper side of FIG. 6, and then the primary coil 11 is wound along the peripheral surface of the second rod-shaped portion 32a illustrated at the lower side of FIG. 6. That is, the primary coil 11 is continuously wound in one turn around the second rod-shaped portion 32a in the direction orthogonal to the axial direction of the second rod-shaped portion 32a.

In this way, the second three-dimensional body 52 is formed by the primary coil 11 wound around the second three-dimensional body formation part 32 and spatially arranged (in a cubic body in this example). FIG. 6 is a schematic perspective view of this state. Accordingly, the second three-dimensional body formation step is completed.

The primary coil is wound once around the second rod-shaped portions with reference signs 32a and 32d, and the primary coil is wound twice around the second rod-shaped portions with reference signs 32b and 32c. The primary coil 11 arranged in the second rod-shaped portions forms the corresponding segments of the second three-dimensional body. In addition, the primary coil 11 is unicursally wound around the second three-dimensional body formation part 32.

As described above, after being wound around the first three-dimensional body formation part 31 to form the first three-dimensional body 51, the rest of the primary coil 11 is first wound around the close second rod-shaped portion, and then the primary coil 11 is further wound around the plurality of second rod-shaped portions. When the primary coil 11 reaches the connected site between the currently wound second rod-shaped portion and the adjacent second rod-shaped portion, the primary coil 11 is wound around the adjacent second rod-shaped portion or the current second rod-shaped portion depending on a choice made between: (i) changing the direction of winding to wind around the adjacent second rod-shaped portion; and (ii) winding continuously around the current second rod-shaped portion. Then, each time the primary coil reaches the connected site between the current second rod-shaped portion and the adjacent second rod-shaped portion, the foregoing choice is made to wind the primary coil 11 around the second three-dimensional body formation part 32 of the mandrel 30 up to a second three-dimensional body terminal end 43 of the primary coil 11.

A coupling element part 54 may be provided between the first three-dimensional body 51 and the second three-dimensional body 52 of the primary coil 11. Accordingly, when the second three-dimensional body 52 is arranged in the hollow portion inside the first three-dimensional body 51 at the inside arrangement step, it is easy to prevent deformation of the first three-dimensional body 51 and the second three-dimensional body 52. In addition, it is easy to arrange the second three-dimensional body 52 in the hollow portion inside the first three-dimensional body 51.

In the example of the mandrel 30 illustrated in FIG. 3, the length of the coupling element part 54 can be adjusted as appropriate by adjusting the axial lengths of the first rod-shaped portion with reference sign 31b of the first three-dimensional body formation part 31 and the second rod-shaped portion with reference sign 32d of the second three-dimensional body formation part 32 or providing an appropriate slack in the primary coil 11 between the first three-dimensional body 51 formed by the first three-dimensional body formation part 31 and the second three-dimensional body 52 formed by the second three-dimensional body formation part 32.

After the completion of the second three-dimensional body formation step, the terminal end of the core wire 38 is fixed as necessary to the second three-dimensional body formation part 32 of the mandrel 30 (not illustrated), and the primary coil 11 including the core wire 38 and the mandrel 30 are heated to fix the shapes of the first three-dimensional body 51 and the second three-dimensional body 52 to the primary coil 11 wound around the mandrel 30. The heating conditions can be decided as appropriate depending on the material for the primary coil 11. For example, the heating temperature is preferably 400° C. or more, and the heating time is preferably 15 minutes or more. After that, the primary coil 11 including the core wire 38 is removed from the mandrel 30 to obtain the intermediate-shape coil 12 given the shape as illustrated in FIG. 7A.

As understood from the foregoing steps, the intermediate-shape coil 12 is formed from the one continuous primary coil 11 and has the first three-dimensional body 51 and the second three-dimensional body 52. The first three-dimensional body 51 and the second three-dimensional body 52 are coupled together via the coupling element part 54. In addition, for each of the first three-dimensional body 51 and the second three-dimensional body 52, the same model structure as the three-dimensional body 20 illustrated in FIG. 2A can be generally assumed, and therefore the same virtual three-dimensional model as the cubic body 22 illustrated in FIG. 2B can be assumed.

In the first three-dimensional body 51, two segments 51a and 51d formed in circles by winding the primary coil 11 once in a circular form and two segments 51b and 51c formed in circles by winding the primary coil 11 twice in a semi-circular (semi-arc) form are aligned in a loop and are spatially arranged in a cubic body shape. The four segments (51a, 51b, 51c, and 51d) are aligned in a cylindrical shape to form the loop part of the first three-dimensional body 51, and the loop part has a central axis 57 in a direction orthogonal to the direction in which the segments (51a, 51b, 51c, and 51d) are aligned in a loop. In addition, the loop part has a hollow portion 261 therein opened on the both sides in the direction of the central axis 57. Further, as in the models illustrated in FIGS. 2A and 2B, an upper opening surface 55 is assumed at the opening of the loop part illustrated at the upper side of FIG. 7A.

The second three-dimensional body 52 is formed by the rest of the primary coil 11 after the formation of the first three-dimensional body 51. In the second three-dimensional body 52, one segment 52a formed in a circle by winding the primary coil 11 once in a circle and winding the primary coil 11 once in an about ⅜ circle (about ⅜ arc), one segment 52d formed in a circle by winding the primary coil 11 once in a circle, and two segments 52b and 52c formed in circles by winding the primary coil 11 twice in a semi-circle (semi-arc) are aligned in a loop and are spatially arranged in a cubic body shape. The four segments (52a, 52b, 52c, and 52d) are aligned in a cylindrical shape to form the loop part of the second three-dimensional body 52, and the loop part has a central axis 58 in a direction orthogonal to the direction in which the segments (52a, 52b, 52c, and 52d) are aligned in a loop. In addition, the loop part has a hollow portion 262 therein opened on the both sides in the direction of the central axis 58. Further, as in the models illustrated in FIGS. 2A and 2B, an upper opening surface 56 is assumed at the opening of the loop part illustrated at the upper side of FIG. 7A.

The core wire 38 is preferably not removed from the intermediate-shape coil 12 to maintain the shape of the intermediate-shape coil 12 at the inside arrangement step described later. FIG. 7A does not illustrate the core wire for the sake of convenience.

In the present invention, after the completion of the second three-dimensional body formation step, the inside arrangement step is performed to arrange one of the first and second three-dimensional bodies inside the loop part of the plurality of segments aligned in a loop of the other three-dimensional body. In this example, the case in which, out of the first three-dimensional body 51 and the second three-dimensional body 52 in the similarity relationship illustrated in FIG. 7A, the second three-dimensional body 52 smaller than the first three-dimensional body 51 is arranged in the hollow portion 261 inside the first three-dimensional body 51 will be described.

First, as illustrated in FIG. 7A, the intermediate-shape coil 12 is arranged such that the upper opening surface 55 of the first three-dimensional body 51 and the upper opening surface 56 of the second three-dimensional body 52 in the intermediate-shape coil 12 face toward the upper side of FIG. 7A. Next, as illustrated in FIG. 7B, the second three-dimensional body 52 is moved to the upper side of the first three-dimensional body 51 such that the central axis 58 of the second three-dimensional body 52 is collinear with the central axis 57 of the first three-dimensional body 51. At this time, the first three-dimensional body 51 and the second three-dimensional body 52 are arranged such that, in the regular square recognized in the cross-sectional direction orthogonal to the central axis 57 of the first three-dimensional body 51 and the regular square recognized in the cross-sectional direction orthogonal to the central axis 58 of the second three-dimensional body 52, the sides of the regular squares are parallel to each other. That is, the first three-dimensional body 51 and the second three-dimensional body 52 are arranged such that the sides formed by the segments with reference signs 51a and 52a, 51b and 52b, 51c and 52c, and 51d and 52d of the first three-dimensional body 51 and the second three-dimensional body 52 are parallel to each other.

Then, as illustrated in FIG. 7C, the second three-dimensional body 52 is axially rotated relative to the first three-dimensional body 51 at a desired angle around the central axis 58 of the second three-dimensional body 52. At this time, the second three-dimensional body 52 is preferably axially rotated such that, in the regular square recognized in the cross-sectional direction orthogonal to the central axis 57 of the first three-dimensional body 51 and the regular square recognized in the cross-sectional direction orthogonal to the central axis 58 of the second three-dimensional body 52, the sides of the regular squares are not parallel.

In the state in which the second three-dimensional body 52 is axially rotated relative to the first three-dimensional body 51 as described above, the second three-dimensional body 52 is arranged in the hollow portion 261 inside the first three-dimensional body 51 as illustrated in FIG. 7D.

Accordingly, the inside arrangement step is completed.

The positional relationship between the first three-dimensional body 51 and the second three-dimensional body 52 illustrated in FIG. 7D will be described with reference to FIG. 7E.

FIG. 7E is a projection diagram illustrating a first regular square 61 and a second regular square 62 formed by projecting the first three-dimensional body 51 and the second three-dimensional body 52 onto a plane 59 (see also FIG. 7D) parallel to the opening surfaces (55 and 56) of the two three-dimensional bodies (51 and 52), that is, orthogonal to the central axes 57 and 58 after the completion of the inside arrangement step, and is cross-sectional view of the shapes recognized in the direction orthogonal to the central axes of the two three-dimensional bodies. A regular square 60 corresponding to the first three-dimensional body 51 has sides (60a, 60b, 60c, and 60d) corresponding to the segments (51a, 51b, 51c, and 51d) of the first three-dimensional body 51 and a loop part formed by the sides. The regular square 61 corresponding to the second three-dimensional body 52 has sides (61a, 61b, 61c, and 61d) corresponding to the segments (52a, 52b, 52c, and 52d) of the second three-dimensional body 52 and a loop part formed by the sides. The regular square 61 is smaller than the regular square 60 and is in a similarity relationship with the regular square 60. The two three-dimensional bodies (51 and 52) are arranged such that the sides of the two regular squares (60 and 61) are not parallel. Accordingly, the second three-dimensional body 52 tends to be easily fixed to the first three-dimensional body 51 as compared to the case where the sides are parallel. There is no particular limitation on the degree to which the sides are not parallel. For example, an angle α formed by two line segments (62a and 63a) extended from a vertex with reference sign 62 of the regular square 60 and a corresponding vertex with reference sign 63 of the regular square 61 toward the central axes 57 and 58 may be larger than 0 degree and smaller than 90 degrees, larger than 90 degrees and smaller than 180 degrees, larger than 180 degrees and smaller than 270 degrees, or larger than 270 degrees and smaller than 360 degrees. However, the angle α is preferably larger than 15 degrees and smaller than 75 degrees to suppress deformation of the first three-dimensional body 51 and the second three-dimensional body 52 due to displacement of the connected site between the two three-dimensional bodies, and to improve workability at the time of arrangement.

The second three-dimensional body 52 may not necessarily be arranged relative to the first three-dimensional body 51 at the inside arrangement step such that the second three-dimensional body 52 is rotated around the central axes 57 and 58 as illustrated in FIGS. 7A to 7D but may be arranged such that the central axes 57 and 58 cross or twist each other. FIG. 8A illustrates an example of case where the first three-dimensional body 51 and the second three-dimensional body 52 are arranged such that the central axis 57 of the first three-dimensional body 51 and the central axis 58 of the second three-dimensional body 52 cross each other after the completion of the inside arrangement step.

FIG. 8A illustrates the state in which, after the first three-dimensional body 51 and the second three-dimensional body 52 are placed in the positional relationship illustrated in FIG. 7B, the second three-dimensional body 52 is arranged in the hollow portion 261 in the first three-dimensional body 51 such that the central axis 58 of the second three-dimensional body 52 is rotated along a plane parallel to planes formed by the segments with reference signs 51d and 51b of the first three-dimensional body 51 including the central axis 57 of the first three-dimensional body 51 to cross the central axis 57 of the first three-dimensional body 51 and the central axis 58 of the second three-dimensional body 52, and planes formed by the segments with reference signs 52d and 52b of the second three-dimensional body 52 are parallel to the plane formed by the segments with reference signs 51d and 51b of the first three-dimensional body 51 including the central axis 57 of the first three-dimensional body 51.

FIG. 8B is a projection diagram illustrating a first regular square and a second regular square formed by projecting the first three-dimensional body 51 and the second three-dimensional body 52 onto a plane 68 (see also FIG. 8A) parallel to the planes formed by the segments with reference signs 51d and 51b of the first three-dimensional body 51 and the planes formed by the segments with reference signs 52d and 52b of the second three-dimensional body 52. In FIG. 8B, the same reference signs as those in FIG. 8A are used for the sake of convenience. Therefore, the first regular square corresponding to the first three-dimensional body 51 is indicated with reference sign 51, and the second regular square corresponding to the second three-dimensional body 52 is indicated with reference sign 52. The first regular square 51 illustrated in FIG. 8B has four sides corresponding to the segments 51a and 51c of the first three-dimensional body 51, the upper opening surface 55, and the lower opening surface 55a, and the plane surrounded by the four sides corresponds to the segment 51b or 51d of the first three-dimensional body 51. In addition, the first regular square 51 has a central axis 57 corresponding to the central axis of the first three-dimensional body 51. The second regular square 52 illustrated in FIG. 8B has four sides corresponding to the segments 52a and 52c of the second three-dimensional body 52, the upper opening surface 56, and the lower opening surface 56a, and the plane surrounded by the four sides corresponds to the segment 52b or 52d of the second three-dimensional body 52. The second regular square 52 also has a central axis 58 corresponding to the central axis of the second three-dimensional body 52.

As illustrated in FIG. 8B, the central axis 57 of the first regular square 51 and the central axis 58 of the second regular square 52 cross each other at a central point 271 of the two regular squares, and cross each other at a central point (not illustrated) of the first three-dimensional body 51 and the second three-dimensional body 52. In the relationship illustrated in FIG. 8B, there is no particular limitation on a crossing angle β of the central axis 58 relative to the central axis 57 as far as the two central axes do not align or parallel with each other. The crossing angle β may be larger than 0 degree and smaller than 180 degrees or larger than 180 degrees and smaller than 360 degrees. However, the crossing angle β is preferably larger than 15 degrees and smaller than 75 degrees to suppress deformation of the first three-dimensional body 51 and the second three-dimensional body 52 due to displacement of the connected site between the two three-dimensional bodies, and to improve workability at the time of arrangement. The crossing angle β illustrated in FIG. 8B means an angle formed when, with respect to the central axis 57 (the upper side of the central point 271 in FIG. 8B), the central axis 58 (the upper side of the central point 271 in FIG. 8B) is rotated clockwise around the central point 271.

All the segments of the first three-dimensional body and the second three-dimensional body may be formed by arranging the primary coil two-dimensionally as illustrated in FIG. 7A. Alternatively, the segments may include any three-dimensionally arranged segment. FIGS. 9 to 11 illustrate the cases where the three-dimensional bodies include a segment formed by arranging the primary coil three-dimensionally.

FIG. 9 is a schematic perspective view of the state after the second three-dimensional body formation step with the use of an example of mandrel capable of setting one of the four segments constituting the first three-dimensional body by arranging the primary coil three-dimensionally.

A mandrel 301 illustrated in FIG. 9 has a first three-dimensional body formation part 331 for forming a first three-dimensional body 351 (see FIG. 10) and a second three-dimensional body formation part 332 for forming a second three-dimensional body 352 (see FIG. 10), and these parts are connected together. The first three-dimensional body formation part 331 has four first rod-shaped portions (331a, 331b, 331c, and 331d). The first rod-shaped portions (331a, 331b, 331c, and 331d) are annularly arranged such that axial directions of the first rod-shaped portions face in a radial direction and are integrated at a crossover site. The second three-dimensional body formation part 332 has four second rod-shaped portions (332a, 332b, 332c, and 332d). The second rod-shaped portions (332a, 332b, 332c, and 332d) are annularly arranged such that axial directions of the second rod-shaped portions face in a radial direction and are integrated at a crossover site. In this example, the one first rod-shaped portion 331d of the four first rod-shaped portions in the first three-dimensional body formation part 331 and the one second rod-shaped portion 332b of the four second rod-shaped portions in the second three-dimensional body formation part 332 are coupled together. In addition, the two parts are connected such that a central axis of the first rod-shaped portions 331b and 331d and a central axis of the second rod-shaped portions 332b and 332d are aligned with each other in the axial direction. The first rod-shaped portions (331a, 331b, 331c, and 331d) and the second rod-shaped portions (332a, 332b, 332c, and 332d) are orthogonal to each other in a cross shape and are all circular in cross section.

In this example, the one first rod-shaped portion 331b of the four first rod-shaped portions (331a, 331b, 331c, and 331d) forms a segment arranged three-dimensionally. The first rod-shaped portion 331b has a large-diameter portion 335, a tapered portion 334, and a small-diameter portion 333 in the order of proximity to the crossover site of the first rod-shaped portions. The large-diameter portion 335 has the same outer diameter as that of the other first rod-shaped portions 331a, 331c, and 331d, and the small-diameter portion 333 has an outer diameter smaller than that of the large-diameter portion 335. The tapered portion 334 is gradually decreased in diameter from the large-diameter portion 335 and continued to the small-diameter portion 333. By changing the outer diameter of the rod-shaped portion as described above, it is possible to form the segment in which the primary coil is arranged three-dimensionally with changes in diameter.

The structures of the first three-dimensional body formation part and the second three-dimensional body formation part can be selected as appropriate depending on the desired shapes of the first and second three-dimensional bodies. The shapes of the three-dimensional bodies are as described above. The position of the rod-shaped portion for forming the segment with the primary coil arranged three-dimensionally can also be selected as appropriate but the rod-shaped portion is preferably provided at the position where winding of the primary coil of the first three-dimensional body is started or the position where winding of the primary coil of the second three-dimensional body is ended. This is because, by providing the three-dimensionally arranged segment at one end of the primary coil, the segment with the primary coil arranged three-dimensionally can be first inserted into an aneurysm in a biological lumen at the time of insertion of the in vivo indwelling member, and the tip of the primary coil inserted into the aneurysm plays the role of an anchor and is easy to fix to the aneurysm wall when it is restored to the secondary shape, thereby facilitating the subsequent insertion of the primary coil into the aneurysm.

The widths or outer diameters of the first rod-shaped portions (331a, 331b, 331c, and 331d) and the second rod-shaped portions (332a, 332b, 332c, and 332d) in the direction orthogonal to the axial direction can be selected as appropriate depending on the purpose of use of the in vivo indwelling member, and the shapes and structures of the first three-dimensional body and the second three-dimensional body.

The sizes, that is, the widths or outer diameters of the rod-shaped portions and the size of the crossover site of the rod-shaped portions of the first three-dimensional body formation part and the second three-dimensional body formation part are preferably different to make it easy to arrange one of the first and second three-dimensional bodies inside the loop part of the other three-dimensional body.

In addition, the first three-dimensional body formation part and the second three-dimensional body formation part are preferably structured such that, when the first three-dimensional body and the second three-dimensional body are formed in polygonal cylinders by these formation parts, the shapes of the polygons recognized in the cross-sectional directions orthogonal to the central axes of the two three-dimensional bodies are in a similarity relationship. In this example, however, for the three-dimensionally arranged segment of the first three-dimensional body, the shape of the polygon is recognized with focus set only on virtual planes assumed at the portion facing the inside of the loop part. Unless otherwise specified, the following description of this example will be provided with focus set only on the virtual planes.

In the example of the mandrel 301 illustrated in FIG. 9, the three first rod-shaped portions (331a, 331c, and 331d) and the large-diameter portion 335 of the one first rod-shaped portion 331b of the first three-dimensional body formation part 331 are equal in outer diameter, and the second rod-shaped portions (332a, 332b, 332c, and 332d) of the second three-dimensional body formation part 332 are equal in outer diameter. However, the first rod-shaped portions (331a, 331c, and 331d) and the large-diameter portion 335 of the first rod-shaped portion 331b are smaller in outer diameter than the second rod-shaped portions (332a, 332b, 332c, and 332d). Accordingly, the first three-dimensional body formation part 31 is larger than the second three-dimensional body formation part 32. Therefore, as for the sizes of the first three-dimensional body 351 and the second three-dimensional body 352 formed by the first three-dimensional body formation part 31 and the second three-dimensional body formation part 32, the first three-dimensional body 351 is smaller than the second three-dimensional body 352. In addition, as for the shapes of the portions of the first three-dimensional body formation part 331 and the second three-dimensional body formation part 332 around which the primary coil 11 is wound, the polygons recognized in planes including the central axis of the first and second rod-shaped portions are regular squares in a similarity relationship. The first three-dimensional body 351 and the second three-dimensional body 352 formed by the formation parts are also in a similarity relationship.

Examples of a first three-dimensional body formation step, a second three-dimensional body formation step, and an inside arrangement step in the case where the primary coil 11 illustrated in FIG. 1C is wound around the mandrel 301 illustrated in FIG. 9, for example, will be described.

At the first three-dimensional body formation step, first, a core wire (not illustrated) longer than the entire primary coil 11 is preferably inserted into the lumen of the primary coil 11. Then, as described above, while one end of the core wire is fixed to a desired position on the mandrel 301 and is placed under tension, for example, the primary coil 11 is wound around the first rod-shaped portion 331b of the mandrel 301. In the example of FIG. 9, one end of the primary coil 11 (with reference sign 340, see FIG. 10) is arranged on the peripheral surface of the small-diameter portion 333 of the first rod-shaped portion 331b at a position (not illustrated) corresponding to the connected site between the first rod-shaped portion 331b and the first rod-shaped portion 331c, and the primary coil 11 is wound in about one turn (360 degrees) along the peripheral surface of the small-diameter portion 333 in the direction orthogonal to the axial direction of the first rod-shaped portion 331b. Then, the primary coil 11 is spirally wound in an about half turn around the peripheral surface at the lower side of FIG. 9 from the tapered portion 334 to the large-diameter portion 335, and the primary coil 11 reaches the connected site between the first rod-shaped portion 331b and the first rod-shaped portion 331a. Then, the direction of winding the primary coil 11 is changed, and the primary coil 11 is wound along the peripheral surface of the first rod-shaped portion 331a illustrated at the upper side of FIG. 9.

At the first rod-shaped portion 331a illustrated at the upper side of FIG. 9, the primary coil 11 is wound about 180 degrees from the connected site between the first rod-shaped portion 331b and the first rod-shaped portion 331a in the direction orthogonal to the axial direction of the first rod-shaped portion 331a, and then the primary coil 11 reaches the connected site between the first rod-shaped portion 331a and the first rod-shaped portion 331d. Then, the direction of winding the primary coil 11 is changed, and the primary coil 11 is wound along the peripheral surface of the first rod-shaped portion 331d illustrated at the lower side of FIG. 9, and then the primary coil 11 is wound along the peripheral surface of the first rod-shaped portion 331d illustrated at the upper side of FIG. 9. That is, the primary coil 11 is continuously wound in one turn around the first rod-shaped portion 331*d* in the direction orthogonal to the axial direction of the first rod-shaped portion 331*d*.

In this manner, when the primary coil 11 is continuously wound in one turn around the first rod-shaped portion 331*d*, the primary coil 11 returns to the connected site between the first rod-shaped portion 331*a* and the first rod-shaped portion 331*d*. Then, the direction of winding the primary coil 11 is changed, and the primary coil 11 is wound along the peripheral surface of the first rod-shaped portion 331*a* illustrated at the lower side of FIG. 9.

At the first rod-shaped portion 331*a* illustrated at the lower side of FIG. 9, the primary coil 11 is wound about 180 degrees from the connected site between the first rod-shaped portion 331*a* and the first rod-shaped portion 331*d* in the direction orthogonal to the axial direction of the first rod-shaped portion 331*a*, and the primary coil 11 returns to the connected site between the first rod-shaped portion 331*a* and the first rod-shaped portion 331*b*. Then, the direction of winding the primary coil 11 is changed, and the primary coil 11 is wound along the peripheral surface of the large-diameter portion 335 of the first rod-shaped portion 331*b* illustrated at the upper side of FIG. 9.

At the large-diameter portion 335 of the first rod-shaped portion 331*b* illustrated at the upper side of FIG. 9, the primary coil 11 is wound about 180 degrees from the connected site between the first rod-shaped portion 331*a* and the first rod-shaped portion 331*b* in the direction orthogonal to the axial direction of the first rod-shaped portion 331*b*, and the primary coil 11 reaches the connected site between the first rod-shaped portion 331*b* and the first rod-shaped portion 331*c*. Then, the direction of winding the primary coil 11 is changed, and the primary coil 11 is wound along the peripheral surface of the first rod-shaped portion 331*c* illustrated at the lower side of FIG. 9.

At the first rod-shaped portion 331*c* illustrated at the lower side of FIG. 9, the primary coil 11 is wound about 180 degrees from the connected site between the first rod-shaped portion 331*b* and the first rod-shaped portion 331*c* in the direction orthogonal to the axial direction of the first rod-shaped portion 331*c*, and the primary coil 11 reaches a portion near the connected site between the first rod-shaped portion 331*c* and the first rod-shaped portion 331*d*. Accordingly, the first three-dimensional body formation step is completed.

As described above, the primary coil is wound once around the first rod-shaped portions with reference signs 331*c* and 331*d*, and the primary coil is wound twice around the first rod-shaped portions with reference signs 331*a* and 331*b*. The primary coil 11 arranged at these first rod-shaped portions forms the corresponding segments of the three-dimensional body. In this example, the primary coil 11 is spirally wound between the two portions where the primary coil 11 is wound in the same plane around the first rod-shaped portion with reference sign 331*b* to form the segment 351*b* in which the primary coil 11 is three-dimensionally arranged (see FIG. 10).

In this example as well, the primary coil 11 is unicursally wound around the first three-dimensional body formation part 331.

After the completion of the first three-dimensional body formation step, the second three-dimensional body formation step is performed to wind the rest of the primary coil 11 after the formation of the first three-dimensional body 351 around the second rod-shaped portions (332*a*, 332*b*, 332*c*, and 332*d*) of the second three-dimensional body formation part 332 and form the second three-dimensional body by the rest of the primary coil 11.

At the second three-dimensional body formation step, first, the primary coil 11 is wound around the second rod-shaped portion 332*c* that has an axial direction parallel to the axial direction of the first rod-shaped portion 331*c* of the first three-dimensional body formation part 331 and is close to the second three-dimensional body formation part 332. The primary coil 11 is preferably wound with tension applied to the core wire extending outward from the other end of the primary coil 11 not illustrated in the same manner as at the first three-dimensional body formation step.

In the example of FIG. 9, after being wound along the peripheral surface of the first rod-shaped portion 331*c* of the first three-dimensional body formation part 331 illustrated at the lower side of FIG. 9, the primary coil 11 is wound from a portion near the connected site between the second rod-shaped portion 332*b* and the second rod-shaped portion 332*c* along the peripheral surface of the second rod-shaped portion 331*c* of the second three-dimensional body formation part 332 illustrated at the upper side of FIG. 9. Then, the primary coil 11 is wound in the direction orthogonal to the axial direction of the second rod-shaped portion 332*c* at the second rod-shaped portion 332*c* illustrated at the upper side of FIG. 9, and then the primary coil 11 is wound along the peripheral surface of the second rod-shaped portion 332*c* illustrated at the lower side of FIG. 9. That is, the primary coil 11 is continuously wound in one turn around the second rod-shaped portion 332*c* in the direction orthogonal to the axial direction of the second rod-shaped portion 332*c*.

In this manner, when the primary coil 11 is continuously wound in one turn around the second rod-shaped portion 332*c*, the primary coil 11 returns to the connected site between the second rod-shaped portion 332*c* and the second rod-shaped portion 332*b*. Then, the direction of winding the primary coil 11 is changed, and the primary coil 11 is wound along the peripheral surface of the second rod-shaped portion 332*b* illustrated at the upper side of FIG. 9.

At the second rod-shaped portion 332*c* illustrated at the upper side of FIG. 9, the primary coil 11 is wound about 180 degrees from the connected site between the second rod-shaped portion 332*c* and the second rod-shaped portion 332*b* in the direction orthogonal to the axis direction of the second rod-shaped portion 332*b*, and the primary coil 11 reaches the connected site between the second rod-shaped portion 332*b* and the second rod-shaped portion 332*a*. Then, the direction of winding the primary coil 11 is changed, and the primary coil 11 is wound along the peripheral surface of the second rod-shaped portion 332*a* illustrated at the lower side of FIG. 9.

At the second rod-shaped portion 332*a* illustrated at the lower side of FIG. 9, the primary coil 11 is wound about 180 degrees from the connected site between the second rod-shaped portion 332*b* and the second rod-shaped portion 332*a* in the direction orthogonal to the axial direction of the second rod-shaped portion 332*a*, and the primary coil 11 reaches the connected site between the second rod-shaped portion 332*a* and the second rod-shaped portion 332*d*. Then, the direction of winding the primary coil 11 is changed, and the primary coil 11 is wound along the peripheral surface of the second rod-shaped portion 332*d* illustrated at the upper side of FIG. 9, and then the primary coil 11 is continuously wound along the peripheral surface of the second rod-shaped portion 332*d* illustrated at the lower side of FIG. 9. That is, the primary coil 11 is continuously wound in one turn around the second rod-shaped portion 332*d* in the direction orthogonal to the axial direction of the second rod-shaped portion 332*d*.

In this manner, when the primary coil 11 is continuously wound in one turn around the second rod-shaped portion 332d, the primary coil 11 returns to the connected site between the second rod-shaped portion 332d and the second rod-shaped portion 332a. Then, the direction of winding the primary coil 11 is changed, and the primary coil 11 is wound along the peripheral surface of the second rod-shaped portion 332a illustrated at the upper side of FIG. 9.

At the second rod-shaped portion 332a illustrated at the upper side of FIG. 9, the primary coil 11 is wound about 180 degrees from the connected site between the second rod-shaped portion 332d and the second rod-shaped portion 332a in the direction orthogonal to the axis direction of the second rod-shaped portion 332a, and the primary coil 11 returns to the connected site between the second rod-shaped portion 332a and the second rod-shaped portion 332b. Then, the direction of winding the primary coil 11 is changed, and the primary coil 11 is wound along the peripheral surface of the second rod-shaped portion 332b illustrated at the lower side of FIG. 9.

At the second rod-shaped portion 332b illustrated at the lower side of FIG. 9, the primary coil 11 is wound about 90 degrees from the connected site between the second rod-shaped portion 332a and the second rod-shaped portion 332b in the direction orthogonal to the axial direction of the second rod-shaped portion 332b.

In this way, the second three-dimensional body 352 is formed by the primary coil 11 wound around the second three-dimensional body formation part 332 and spatially arranged (in a cubic body in this example). FIG. 9 is a schematic perspective view of this state. Accordingly, the second three-dimensional body formation step is completed.

The primary coil is wound once around the second rod-shaped portions with reference signs 332c and 332d, and the primary coil is wound twice around the first rod-shaped portions with reference signs 332a and 332b as described above. The primary coil 11 arranged at the second rod-shaped portions forms the corresponding segments of the second three-dimensional body. In addition, the primary coil 11 is unicursally wound around the second three-dimensional body formation part 332.

In the example of FIG. 9 as well, a coupling element 354 may be provided between the first three-dimensional body 351 and the second three-dimensional body 352 of the primary coil 11. In addition, the length of the coupling element 354 can be adjusted in such a manner as described above.

After the completion of the second three-dimensional body formation step, the primary coil 11 including the core wire and the mandrel 301 are heated to fix the shapes of the first three-dimensional body 351 and the second three-dimensional body 352 to the primary coil 11 wound around the mandrel 301. After that, the primary coil 11 including the core wire is removed from the mandrel 301 to obtain an intermediate-shape coil 121 given the shape as illustrated in FIG. 10.

As understood from the foregoing steps, the intermediate-shape coil 121 is formed from the one continuous primary coil 11 and has the first three-dimensional body 351 and the second three-dimensional body 352. The first three-dimensional body 351 and the second three-dimensional body 352 are coupled together via the coupling element 354. For the second three-dimensional body 352, the same model structure as the three-dimensional body 20 illustrated in FIG. 2A can be generally assumed, and therefore the same virtual three-dimensional model as the cubic body 22 illustrated in FIG. 2B can be assumed. In the first three-dimensional body 351, as for the segment 351b formed by the first rod-shaped portion 331b in which the primary coil 11 is three-dimensionally arranged, a plane including the portion at which the primary coil 11 is wound around the large-diameter portion 335 of the first rod-shaped portion 331b is assumed as virtual plane described above. Then, the same model structure as the three-dimensional body 20 illustrated in FIG. 2A is assumed with focus set only on the virtual plane.

In the first three-dimensional body 351, one segment 351a formed in a circle by winding the primary coil 11 twice in a semi-circle (semi-arc), one segment 351b formed in a three-dimensional shape by winding the primary coil 11 once in an arc and subsequently winding the primary coil 11 in a half turn in a spiral, and then winding the primary coil 11 once in a semi-circle (semi-arc), one segment 351c formed in an about ⅜ circle (about ⅜ arc) by winding the primary coil 11 once in an about ⅜ circle (about ⅜ arc), and one segment 351d formed in a circle by winding the primary coil 11 once in a circle are aligned in a loop and are spatially arranged in a cubic body shape. The primary coil is arranged two-dimensionally in the segments 351a, 351c, and 351d, and is arranged three-dimensionally in the segment 351b. The four segments (351a, 351b, 351c, and 351d) are aligned in a cylindrical shape to form the loop part of the first three-dimensional body 351, and the loop part has a central axis 357 in a direction orthogonal to the direction in which the segments (351a, 351b, 351c, and 351d) are aligned in a loop. In addition, the loop part has a hollow portion 326 therein opened on the both sides in the direction of the central axis 357. Further, as in the models illustrated in FIGS. 2A and 2B, an upper opening surface 355 is assumed at the opening of the loop part illustrated at the upper side of FIG. 10.

The second three-dimensional body 352 is formed by the rest of the primary coil 11 after the formation of the first three-dimensional body 351. In the second three-dimensional body 352, one segment 352a formed in a circle by winding the primary coil 11 twice in a semi-circle (semi-arc), one segment 352b formed in an arc by winding the primary coil 11 once in a semi-circle (semi-arc) and winding the primary coil 11 once in an about ¼ circle (about ¼ arc), and two segments 352c and 352d formed in circles by winding the primary coil 11 once in a circle are aligned in a loop and are spatially arranged in a cubic body shape. The four segments (352a, 352b, 352c, and 352d) are aligned in a cylindrical shape to form the loop part of the second three-dimensional body 352, and the loop part has a central axis 358 in a direction orthogonal to the direction in which the segments (352a, 352b, 352c, and 352d) are aligned in a loop. In addition, the loop part has a hollow portion 327 therein opened on the both sides in the direction of the central axis 358. Further, as in the models illustrated in FIGS. 2A and 2B, an upper opening surface 356 is assumed at the opening of the loop part illustrated at the upper side of FIG. 10.

After the completion of the second three-dimensional body formation step, the inside arrangement step is performed to arrange one of the first three-dimensional body 351 and the second three-dimensional body 352 inside the loop part of the plurality of segments aligned in a loop of the other three-dimensional body. As described above, the core wire not illustrated is preferably not removed from the intermediate-shape coil 12. FIGS. 9 and 10 do not illustrate the core wire for the sake of convenience.

In this example, in the same manner as illustrated in FIGS. 7A to 7E, while the first three-dimensional body 351 is axially rotated relative to the second three-dimensional body 352, out of the first three-dimensional body 351 and the second three-dimensional body 352 in the similarity relationship illustrated in FIG. 10, the first three-dimensional body 351 smaller than the second three-dimensional body 352 is arranged in the hollow portion 327 inside the second three-dimensional body 352. FIG. 11 is a schematic perspective view of this state. As for the segment 351b of the first three-dimensional body 351, the similarity relationship between the first three-dimensional body 351 and the second three-dimensional body 352 does not cover the entire structure of the primary coil arranged three-dimensionally but indicates the relationship focusing only on the virtual plane described above.

After the completion of the inside arrangement step, the intermediate-shape coil 12 or 121 with the second three-dimensional body 52 inside the first three-dimensional body 51 as illustrated in FIG. 7D, 8A, or 11 is heated to fix the shape in which the second three-dimensional body 52 is arranged inside the first three-dimensional body 51 as secondary shape to the primary coil 11. The heating conditions can be decided as appropriate depending on the material for the primary coil 11. For example, the heating temperature is preferably 400° C. or higher, and is desirably higher than the heating temperature for giving the intermediate shape to the primary coil 11 as described above. The heating time is preferably 15 minutes or more.

After that, the core wire 38 is removed to give the spatial three-dimensional secondary shape to the primary coil 11 as illustrated in FIG. 7D, 8A, or 11, thereby obtaining the secondary coil 13, 130, or 133.

Second Embodiment

In a second embodiment, a first three-dimensional body formation step and a second three-dimensional body formation step as described above in relation to the first embodiment are performed to form a first three-dimensional body and a second three-dimensional body, then an additional three-dimensional body formation step is performed to form an additional three-dimensional body, and then first and second inside arrangement steps are performed to arrange one three-dimensional body inside loop part of a plurality of segments aligned in a loop in another three-dimensional body, and arrange still other three-dimensional body inside loop part of a plurality of segments aligned in a loop of the another three-dimensional body, for example, whereby the first three-dimensional body, the second three-dimensional body, and the additional three-dimensional body are triply arranged in an arbitrary order. An example of the second embodiment will be described below with reference to FIGS. 12 to 15. However, only the matter specific to the second embodiment will be described but the matter in common with the first embodiment will be omitted with the use of the same reference signs.

In the second embodiment, the same primary coil as described above in relation to the first embodiment can be used. In the following description, the same models as illustrated in FIGS. 2A to 2C will be applied.

In the second embodiment, the same primary coil as described above in relation to the first embodiment is used. First, the first three-dimensional body is formed by winding the primary coil at least once to form a plurality of segments, aligning the segments in a loop, and spatially arranging part of the primary coil (the first three-dimensional body formation step). Then, the second three-dimensional body is formed by spatially arranging at least part of the rest of the primary coil after the formation of the first three-dimensional body (the second three-dimensional body formation step). Further, in the second embodiment, the additional three-dimensional body is formed by winding the primary coil at least once to form a plurality of segments, aligning the segments in a loop, and spatially arranging at least part of the rest of the primary coil after the formation of the first and second three-dimensional bodies (the additional three-dimensional body formation step).

FIG. 12 is a schematic perspective view of another example of a mandrel usable in the example. A mandrel 300 illustrated in FIG. 12 has a first three-dimensional body formation part 31, a second three-dimensional body formation part 32, and an additional three-dimensional body formation part 33, which are connected together. The additional three-dimensional body formation part 33 has four additional rod-shaped portions (33a, 33b, 33c, and 33d). The additional rod-shaped portions (33a, 33b, 33c, and 33d) are annularly arranged such that axial directions of the additional rod-shaped portions face in a radial direction, and are integrated at the crossover sites. In addition, in this example, one second rod-shaped portion 32b of four second rod-shaped portions (32a, 32b, 32c, and 32d) of the second three-dimensional body formation part 32 and one additional rod-shaped portion 33d of four additional rod-shaped portions (33a, 33b, 33c, and 33d) of the additional three-dimensional body formation part 33 are coupled together. The both parts are coupled together such that a central axis of the second rod-shaped portion 32b and a central axis of the additional rod-shaped portion 33d are aligned with each other. The additional three-dimensional body formation part 33 is an example for the formation of the structure of the three-dimensional body 20 illustrated in FIG. 2A as described above, and the additional rod-shaped portions (33a, 33b, 33c, and 33d) are orthogonal to each other in a cross form and are all circular in cross section.

The structure of the additional three-dimensional body formation part can be selected as appropriate depending on the desired shape of the additional three-dimensional body. The shapes of the three-dimensional bodies are as described above in relation to the first and second three-dimensional bodies in the first embodiment. The widths or outer diameters of the additional rod-shaped portions (33a, 33b, 33c, and 33d) in the direction orthogonal to the axial direction can be selected as appropriate depending on the purpose of use of the in vivo indwelling member, and the shape and structure of the additional three-dimensional body. For example, the widths or outer diameters are preferably 1 to 30 mm in the case where the in vivo indwelling member is used for treatment of aneurysm obliteration.

The sizes, that is, the widths or outer diameters of the rod-shaped portions and the size of the crossover site of the rod-shaped portions of the first three-dimensional body formation part and the second three-dimensional body formation part are preferably different from one another to make it easy to arrange, out of the first three-dimensional body, the second three-dimensional body, and the additional three-dimensional body, one three-dimensional body inside the loop part of another three-dimensional body in an arbitrary manner. The three-dimensional bodies arranged more inside are preferably smaller in size.

In addition, the structures of the first three-dimensional body formation part 31, the second three-dimensional body formation part 32, and the additional three-dimensional body formation part 33 are preferably in a similarity relationship because the first three-dimensional body, the second three-dimensional body, and the additional three-dimensional body can be stably maintained in structure when the three-dimensional bodies are arranged as illustrated in FIG. 15, for example.

In the example of the mandrel 300 illustrated in FIG. 12, the configurations of the first three-dimensional body formation part 31 and the second three-dimensional body formation part 32 are described above in relation to the first embodiment. In the additional three-dimensional body formation part 33, the four additional rod-shaped portions (33a, 33b, 33c, and 33d) are equal in outer diameter but are smaller in outer diameter than the second rod-shaped portions (32a, 32b, 32c, and 32d). Accordingly, the first three-dimensional body formation part 31 is larger than the second three-dimensional body formation part 32, and the second three-dimensional body formation part 32 is larger than the additional three-dimensional body formation part 33. Therefore, the first three-dimensional body 51, the second three-dimensional body 52, and the additional three-dimensional body 53 formed by the first three-dimensional body formation part 31, the second three-dimensional body formation part 32, and the additional three-dimensional body formation part 33 become smaller in size in this order. In addition, as for the shapes of the portions of the first three-dimensional body formation part 31, the second three-dimensional body formation part 32, and the additional three-dimensional body formation part 33 around which the primary coil 11 is wound, the polygons recognized in planes including the central axes of the first rod-shaped portions, the second rod-shaped portions, and the additional rod-shaped portions are all regular squares in a similarity relationship. The first three-dimensional body 51, the second three-dimensional body 52, and the additional three-dimensional body 53 formed by the first three-dimensional body formation part 31, the second three-dimensional body formation part 32, and the additional three-dimensional body formation part 33 are also in a similarity relationship.

An example of the first three-dimensional body formation step, the second three-dimensional body formation step, and the additional three-dimensional body formation step will be described taking the case in which the primary coil 11 illustrated in FIG. 1C is wound around the mandrel 300 illustrated in FIG. 12, for example.

The first three-dimensional body formation step and the second three-dimensional body formation step are performed in the same manner as described above in relation to the first embodiment. In this embodiment, however, at the second three-dimensional body formation step, a second three-dimensional body terminal end 43 is not at the other end of the primary coil 11 but is continuous, unlike in the case illustrated in FIG. 6.

After the completion of the second three-dimensional body formation step, the additional three-dimensional body formation step is performed to wind the rest of the primary coil 11 after the formation of the first three-dimensional body 51 and the second three-dimensional body 52 around the additional rod-shaped portions (33a, 33b, 33c, and 33d) of the additional three-dimensional body formation part 33 and form the additional three-dimensional body in the rest of the primary coil 11. FIG. 13 is a schematic perspective view illustrating the state after the additional three-dimensional body formation step.

At the additional three-dimensional body formation step, first, the primary coil 11 is wound around the additional rod-shaped portion 33a of the additional three-dimensional body formation part 33 that has an axial direction parallel to the axial direction of the second rod-shaped portion 32a of the second three-dimensional body formation part 32 and is close to the rest of the primary coil 11 immediately after the second three-dimensional body formation step. The primary coil 11 can be wound with tension applied to the core wire of the primary coil 11 extending outward from the other end not illustrated as at the first three-dimensional body formation step. In the example of FIG. 13, after being wound along the peripheral surface of the second rod-shaped portion 32a of the second three-dimensional body formation part 32 illustrated at the lower side of FIG. 13, the primary coil 11 is wound along the peripheral surface of the second rod-shaped portion 33a of the additional three-dimensional body formation part 33 illustrated at the upper side of FIG. 13. Then, at the additional rod-shaped portion 33a illustrated at the upper side of FIG. 13, the primary coil 11 is wound in the direction orthogonal to the axial direction of the additional rod-shaped portion 33a, and the primary coil 11 reaches the connected site between the additional rod-shaped portion 33a and the additional rod-shaped portion 33b. Then, the direction of winding the primary coil 11 is changed, and the primary coil 11 is wound along the peripheral surface of the additional rod-shaped portion 33b illustrated at the lower side of FIG. 13.

At the additional rod-shaped portion 33b illustrated at the lower side of FIG. 13, the primary coil 11 is wound about 180 degrees from the connected site between the additional rod-shaped portion 33a and the additional rod-shaped portion 33b in the direction orthogonal to the axial direction of the additional rod-shaped portion 33b, and the primary coil 11 reaches the connected site between the additional rod-shaped portion 33b and the additional rod-shaped portion 33c. Then, the direction of winding the primary coil 11 is changed, and the primary coil 11 is wound along the peripheral surface of the additional rod-shaped portion 33c illustrated at the upper side of FIG. 13.

At the additional rod-shaped portion 33c illustrated at the upper side of FIG. 13, the primary coil 11 is wound about 180 degrees from the connected site between the additional rod-shaped portion 33b and the additional rod-shaped portion 33c in the direction orthogonal to the axial direction of the second rod-shaped portion 33c, and the primary coil 11 reaches the connected site between the additional rod-shaped portion 33c and the additional rod-shaped portion 33d. Then, the direction of winding the primary coil 11 is changed, and the primary coil 11 is wound along the peripheral surface of the additional rod-shaped portion 33d illustrated at the lower side of FIG. 13, and then the primary coil 11 is continuously wound along the peripheral surface of the additional rod-shaped portion 33d illustrated at the upper side of FIG. 13. That is, the primary coil 11 is continuously wound in one turn around the additional rod-shaped portion 33d in the direction orthogonal to the axial direction of the additional rod-shaped portion 33d.

When the primary coil 11 is continuously wound in one turn around the additional rod-shaped portion 33d in this way, the primary coil 11 returns to the connected site between the additional rod-shaped portion 33c and the additional rod-shaped portion 33d. Then, the direction of winding the primary coil 11 is changed, and the primary coil 11 is wound along the peripheral surface of the additional rod-shaped portion 33c illustrated at the lower side of FIG. 13.

At the additional rod-shaped portion 33c illustrated at the lower side of FIG. 13, the primary coil 11 is wound about 180 degrees from the connected site between the additional rod-shaped portion 33c and the additional rod-shaped portion 33d in the direction orthogonal to the axial direction of the additional rod-shaped portion 33c, the primary coil 11 returns to the connected site between the additional rod-shaped portion 33b and the additional rod-shaped portion 33c. Then, the direction of winding the primary coil 11 is changed, and the primary coil 11 is wound along the peripheral surface of the additional rod-shaped portion 33b illustrated at the upper side of FIG. 13.

At the additional rod-shaped portion 33b illustrated at the upper side of FIG. 13, the primary coil 11 is wound about 180 degrees from the connected site between the additional rod-shaped portion 33b and the additional rod-shaped portion 33c in the direction orthogonal to the axial direction of the additional rod-shaped portion 33b, and the primary coil 11 returns to the connected site between the additional rod-shaped portion 33a and the additional rod-shaped portion 33b. Then, the direction of winding the primary coil 11 is changed, and the primary coil 11 is wound along the peripheral surface of the additional rod-shaped portion 33a illustrated at the lower side of FIG. 13.

At the additional rod-shaped portion 33a illustrated at the lower side of FIG. 13, the primary coil 11 is wound about 90 degrees from the connected site between the additional rod-shaped portion 33a and the additional rod-shaped portion 33b in the direction orthogonal to the axial direction of the additional rod-shaped portion 33a.

Accordingly, the primary coil 11 is wound around the additional three-dimensional body formation part 33 and spatially arranged (in a cubic body shape in this example) to form the additional three-dimensional body 53. FIG. 13 is a schematic perspective view of this state. Accordingly, the additional three-dimensional body formation step is completed.

As described above, the primary coil is wound once around the additional rod-shaped portion with reference sign 33d, and the primary coil is wound twice around the additional rod-shaped portions with reference signs 33a, 33b, and 33c. The primary coil 11 arranged at the additional rod-shaped portions forms the corresponding segments of the additional three-dimensional body. In addition, the primary coil 11 is unicursally wound around the additional three-dimensional body formation part 33.

As described above, after being wound around the first three-dimensional body formation part 31 and the second three-dimensional body formation part 32 to form the first three-dimensional body 51 and the second three-dimensional body 52, the rest of the primary coil 11 is first wound around the close additional rod-shaped portion, and then the primary coil 11 is further wound around the plurality of additional rod-shaped portions. When the primary coil 11 reaches the connected site between the currently wound additional rod-shaped portion and the adjacent additional rod-shaped portion, the primary coil 11 is wound around the adjacent additional rod-shaped portion or the current additional rod-shaped portion depending on a choice made between: (i) changing the direction of winding to wind around the adjacent additional rod-shaped portion; and (ii) winding continuously around the current additional rod-shaped portion. Then, each time the primary coil 11 reaches the connected site between the current additional rod-shaped portion and the adjacent additional rod-shaped portion, the foregoing choice is made to wind the primary coil 11 around the additional three-dimensional body formation part 33 of the mandrel 30 up to an additional three-dimensional body terminal end 45 of the primary coil 11 (see FIG. 14).

A coupling element part 540 may be provided between the second three-dimensional body 52 and the additional three-dimensional body 53 of the primary coil 11. Accordingly, when the additional three-dimensional body 53 is arranged in the hollow portion inside the second three-dimensional body 52 at the additional three-dimensional body arrangement step, it is easy to prevent deformation of the second three-dimensional body 52 and the additional three-dimensional body 53. In addition, it is easy to arrange the additional three-dimensional body 52 in the hollow portion inside the second three-dimensional body 52.

In the example of the mandrel 300 illustrated in FIG. 12, the length of the coupling element part 540 can be adjusted as appropriate by adjusting the axial lengths of the first rod-shaped portion with reference sign 32b of the second three-dimensional body formation part 32 and the additional rod-shaped portion with reference sign 33d of the additional three-dimensional body formation part 33 or providing an appropriate slack in the primary coil 11 between the second three-dimensional body 52 formed by the second three-dimensional body formation part 32 and the additional three-dimensional body 53 formed by the additional three-dimensional body formation part 33.

After the completion of the second three-dimensional body formation step, the terminal end of the core wire is fixed as necessary to the additional three-dimensional body formation part 33 of the mandrel 300 (not illustrated), and the primary coil 11 including the core wire and the mandrel 300 are heated to fix the shapes of the first three-dimensional body 51, the second three-dimensional body 52, and the additional three-dimensional body 53 to the primary coil 11 wound around the mandrel 300. The heating conditions can be decided in the same manner as in the first embodiment. After that, the primary coil 11 including the core wire is removed from the mandrel 300 to obtain the intermediate-shape coil 120 given the shape as illustrated in FIG. 14.

As understood from the foregoing steps, the intermediate-shape coil 120 is formed from the one continuous primary coil 11 and has the first three-dimensional body 51, the second three-dimensional body 52, and the additional three-dimensional body 53. The first three-dimensional body 51 and the second three-dimensional body 52 are coupled together via the coupling element part 54, and the second three-dimensional body 52 and the additional three-dimensional body 53 are coupled together via the coupling element part 540. In addition, for the first three-dimensional body 51, the second three-dimensional body 52, and the additional three-dimensional body 53, the same model structure as the three-dimensional body 20 illustrated in FIG. 2A can be generally assumed, and therefore the same virtual three-dimensional model as the cubic body 22 illustrated in FIG. 2B can be assumed.

The first three-dimensional body 51 and the second three-dimensional body 52 are configured as described above in relation to the first embodiment. The additional three-dimensional body 53 is formed by the rest of the primary coil 11 after the formation of the first three-dimensional body 51 and the second three-dimensional body 52. The additional three-dimensional body 53 has a central axis 272 in a direction orthogonal to the direction in which one segment 53a formed in an about ⅝ circle (about ⅝ arc) by winding the primary coil 11 once in an about ⅜ circle (about ⅜ arc) and winding the primary coil 11 once in an about ¼ circle (about ¼ arc), two segments 53b and 53c formed in circles by winding the primary coil 11 twice in a semi-circle (semi-arc), and one segment 53d formed in a circle by winding the primary coil 11 once in a circle are aligned in a loop. In addition, the loop part has a hollow portion 263 therein opened on the both sides in the direction of the central axis 272. Further, as in the models illustrated in FIGS. 2A and 2B, an upper opening surface 241 is assumed at the opening of the loop part illustrated at the upper side of FIG. 14.

As in the first embodiment, the core wire is preferably not removed from the intermediate-shape coil 120 at first and second inside arrangement steps described later. FIG. 14 does not illustrate the core wire for the sake of convenience.

In the second embodiment, the first inside arrangement step is performed to arrange one of the first three-dimensional body, the second three-dimensional body, and the additional three-dimensional body inside the loop part of the plurality of segments aligned in a loop of one of the two remaining three-dimensional bodies, and the second inside arrangement step is performed to arrange the one remaining three-dimensional body inside the loop part of the plurality of segments aligned in a loop of the three-dimensional body arranged inside at the first inside arrangement step, or arrange the two three-dimensional bodies after the first inside arrangement step inside the loop part of the plurality of segments aligned in a loop of the one remaining three-dimensional body.

In this example, descriptions will be given to the case where, out of the second three-dimensional body 52 and the additional three-dimensional body 53 in the similarity relationship illustrated in FIG. 14, the additional three-dimensional body 53 smaller in size than the second three-dimensional body 52 is arranged in the hollow portion 262 inside the second three-dimensional body 52 at the first inside arrangement step, and the second three-dimensional body 52 with the additional three-dimensional body 53 arranged in the hollow portion 262 after the first inside arrangement step is arranged in the hollow portion 261 inside the first three-dimensional body 51 that is in the similarity relationship with the second three-dimensional body 52 and the additional three-dimensional body 53 and is larger in size than the second three-dimensional body 52 at the second inside arrangement step.

The first inside arrangement step will be described. First, the intermediate-shape coil 120 is arranged such that the upper opening surface 56 of the second three-dimensional body 52 and the upper opening surface 241 of the additional three-dimensional body 53 in the intermediate-shape coil 120 face toward the upper side of FIG. 14 in the same positional relationship as illustrated in FIG. 7A. Next, the additional three-dimensional body 53 is moved to the upper side of the second three-dimensional body 52 such that the central axis 58 of the second three-dimensional body 52 is collinear with the central axis 272 of the additional three-dimensional body 53 in the same positional relationship as illustrated in FIG. 7B. At this time, in the regular square as a shape recognized in the cross-sectional direction orthogonal to the central axis 58 of the second three-dimensional body 52 and the regular square as a shape recognized in the cross-sectional direction orthogonal to the central axis 272 of the additional three-dimensional body 53, the sides of the regular squares are arranged in parallel to each other. Specifically, the second three-dimensional body 52 and the additional three-dimensional body 53 are arranged such that the sides formed by the segments with reference signs 52*a* and 53*a*, 52*b* and 53*b*, 52*c* and 53*c*, and 52*d* and 53*d* of the second three-dimensional body 52 and the additional three-dimensional body 53 are parallel to each other.

In addition, the additional three-dimensional body 53 is axially rotated relative to the second three-dimensional body 52 at a desired angle around the central axis 272 of the additional three-dimensional body 53 in the same positional relationship as illustrated in FIG. 7C. At this time, the additional three-dimensional body 53 is preferably axially rotated such that, in the regular square as a shape recognized in the cross-sectional direction orthogonal to the central axis 58 of the second three-dimensional body 52 and the regular square as a shape recognized in the cross-sectional direction orthogonal to the central axis 272 of the additional three-dimensional body 53, the sides of the regular squares are not parallel to each other.

In the state in which the additional three-dimensional body 53 is axially rotated relative to the second three-dimensional body 52 as described above, the additional three-dimensional body 53 is arranged in the hollow portion 262 inside the second three-dimensional body 52 in the same positional relationship as illustrated in FIG. 7D.

Accordingly, the first inside arrangement step is completed. The positional relationship between the second three-dimensional body 52 and the additional three-dimensional body 53 is the same as illustrated in FIG. 7E. Alternatively, although not illustrated, the additional three-dimensional body 53 and the second three-dimensional body 52 may be arranged in the same manner as illustrated in FIGS. 8A and 8B.

Next, the second inside arrangement step will be performed. At the second inside arrangement step, the second three-dimensional body 52 with the additional three-dimensional body 53 arranged in the hollow portion 262 after the first inside arrangement step is arranged in the hollow portion 261 inside the first three-dimensional body 51. The method for the arrangement can be decided by the positional relationship between the first three-dimensional body 51 and the second three-dimensional body 52 as in the case illustrated in FIGS. 7A to 7E. FIG. 15 is a schematic perspective view of the state after the second inside arrangement step. Alternatively, although not illustrated, the first three-dimensional body 51 and the second three-dimensional body 52 may be arranged in the same manner as illustrated in FIGS. 8A and 8B.

Still alternatively, although not illustrated, the arrangement illustrated in FIGS. 7A to 7E may be used at one of the first inside arrangement step and the second inside arrangement step, and the arrangement illustrated in FIGS. 8A and 8B may be used at the other step.

In the intermediate-shape coil 120 or the secondary coil 131 illustrated in FIG. 15, the second three-dimensional body 52 is arranged inside the first three-dimensional body 51, and the additional three-dimensional body 53 is arranged inside the second three-dimensional body 52. As for the sizes of these three-dimensional bodies, the three-dimensional bodies positioned more inside, that is, the three-dimensional bodies positioned more inside the loop part of the segments aligned in a loop are smaller. In addition, the shapes recognized in the cross-sectional direction orthogonal to the central axes 57, 58, and 272 of the three-dimensional bodies are regular squares in a similarity relationship. Further, the central axes 57, 58, and 272 of the three-dimensional bodies are collinear with one another and arranged such that the sides of the regular squares of the three-dimensional bodies are not parallel.

Instead of the foregoing example, the second three-dimensional body 52 may be arranged in the hollow portion 261 inside the first three-dimensional body 51 at the first inside arrangement step, and the additional three-dimensional body 53 may be arranged in the hollow portion 262 inside the second three-dimensional body 52 at the second inside arrangement step.

After the completion of the second inside arrangement step, in the state in which the second three-dimensional body 52 is arranged inside the first three-dimensional body 51 and the additional three-dimensional body 53 is arranged inside the second three-dimensional body 52 as illustrated in FIG. 15, the intermediate-shape coil 120 is heated to fix the shape in which the second three-dimensional body 52 is arranged inside the first three-dimensional body 51 and the additional three-dimensional body 53 is arranged inside the second three-dimensional body 52 as a secondary shape to the primary coil 11. The heating conditions are the same as those in the first embodiment.

After that, the core wire is removed to obtain the secondary coil 131 in which the primary coil 11 is given the spatial three-dimensional secondary shape as illustrated in FIG. 15.

Other Embodiments

The present invention is not limited to the foregoing embodiments but can be modified in various manners without deviating from the gist of the present invention.

For example, the mandrel 300 illustrated in FIG. 12 has the first three-dimensional body formation part 31, the second three-dimensional body formation part 32, and the additional three-dimensional body formation part 33 aligned in line in this order. That is, the three-dimensional body formation parts are aligned in line such that the sizes of the three-dimensional body formation parts become smaller in this order. However, the present invention is not limited to this but the largest three-dimensional body formation part may be arranged in the center or the smallest three-dimensional body formation part may be arranged in the center.

For example, in the mandrel 300 illustrated in FIG. 12, the first three-dimensional body formation part 31, the second three-dimensional body formation part 32, and the additional three-dimensional body formation part 33 are aligned in line in this order and the primary coil is wound around these three-dimensional body formation parts in this order. However, the present invention is not limited to this but the first three-dimensional body formation part may be provided in the center and the primary coil may be first wound around this central part. In this case, the primary coil moves from the second three-dimensional body formation part to the additional three-dimensional body formation part through the first three-dimensional body formation part, and the first three-dimensional body formation part can serve as a coupling element.

For example, at the first three-dimensional body formation step, the second three-dimensional body formation step, and the additional three-dimensional body formation step, the procedures for winding the primary coil around the mandrel are not limited to the ones illustrated in FIGS. 4 to 6, 9, and 13 but can be decided in an arbitrary manner. The mode in which the primary coil is wound once around one rod-shaped portion is not limited to a single circle formed by winding in a ⅜ arc, a semi-arc, a ¾ arc, and one turn as illustrated in FIGS. 4 to 6, 9, and 13 but may be an arc of another length, one-and-a-half circles formed by winding in one-and-a-half turns, two or multiple circles formed by winding in two or more turns, or the like.

For example, in the foregoing example, after the completion of the first three-dimensional body formation step, the second three-dimensional body formation step, and the additional three-dimensional body formation step, the primary coil is wound around all the rod-shaped portions constituting the first three-dimensional body formation part, the second three-dimensional body formation part, and the additional three-dimensional body formation part. However, the present invention is not limited to this but the primary coil may not be wound around some rod-shaped portion. In this case with the use of the mandrel 30, 301, or 300 as illustrated in FIG. 3, 9, or 12, when the primary coil is not wound around one of the four rod-shaped portions in one three-dimensional body formation part, a triangular cylindrical three-dimensional body is formed.

For example, in the foregoing example, the first three-dimensional body formation step and the second three-dimensional body formation step, or the first three-dimensional body formation step, the second three-dimensional body formation step, and the additional three-dimensional body formation step are performed with one mandrel having the first three-dimensional body formation part, the second three-dimensional body formation part, and as necessary the additional three-dimensional body formation part as illustrated in FIG. 3, 9, or 12. However, the present invention is not limited to this but these three-dimensional body formation steps may be performed with the use of two or more mandrels corresponding to the individual steps.

In the foregoing example, the heating process is performed to heat the intermediate-shape coil after the inside arrangement step in the first embodiment or the second inside arrangement step in the second embodiment to fix the desired secondary shape to the intermediate-shape coil. In the heating process, a secondary shape maintenance jig may be used to fix the secondary shape. There is no particular limitation on the shape and structure of the secondary shape maintenance jig as far as the shape of the intermediate-shape coil given the secondary shape after the inside arrangement step or the second inside arrangement step can be maintained in the heating process. For example, a mold capable of shaping an inner cavity part corresponding to the secondary shape given to the intermediate-shape coil may be used. The shape of the inner cavity part of the mold can be decided according to the secondary shape and may be a prism, a polyhedron such as a regular polyhedron, a circular column, or the like, for example.

[Method for Using the In vivo Indwelling Member]

The thus obtained secondary coil given the secondary shape can be preferably used as an in vivo indwelling member. An example of method for using the in vivo indwelling member having the secondary coil to be inserted into an aneurysm generated in a parent blood vessel will be briefly described.

FIG. 16 is a schematic cross-sectional view of the state in which a delivery catheter 73 for delivering an in vivo indwelling member 132 having the secondary coil (13, 130, 131, or 133) described above is used to insert the in vivo indwelling member 132 into an aneurysm 71 generated in a parent blood vessel 72. For the sake of simplicity, FIG. 16 does not illustrate the coiled shape formed by the wire material of the primary coil (11 or 11a) as illustrated in FIG. 1C or 1D but represents the in vivo indwelling member 132 by flat planes.

The in vivo indwelling member 132 indwells in the aneurysm 71 generated in the parent blood vessel 72 of the living body through the delivery catheter 73 to embolize the aneurysm 71. Accordingly, the in vivo indwelling member 132 is also called embolization coil.

As illustrated in FIG. 16, the in vivo indwelling member 132 is separably coupled to the tip of a delivery wire 74. The delivery wire 74 and the in vivo indwelling member 132 are coupled by a standard method. The in vivo indwelling member 132 coupled to the tip of the delivery wire 74 is inserted into an inner cavity part 75 of the delivery catheter 73. At this time, the in vivo indwelling member 132 is in the state of the primary coil (11 or 11a) extended in a linear fashion as illustrated in FIG. 1C or 1D. The base end side of the delivery wire 74 not illustrated is operated to release the in vivo indwelling member 132 from a tip opening 76 of the delivery catheter 73 and insert the in vivo indwelling member 132 into the aneurysm 71. When released from the tip opening 76 of the delivery catheter 73, the in vivo indwelling member 132 is formed in the spatial three-dimensional secondary shape (13, 130, 131, or 133) as illustrated in FIG. 7D, 8A, 11, or 15 gradually from the released portion. That is, the in vivo indwelling member 132 is restored from the primary shape to the secondary shape. At this time, when the in vivo indwelling member 132 has the secondary shape 133 as illustrated in FIG. 11 and the segment of the first three-dimensional body 351 with the three-dimensionally arranged primary coil is provided at the end portion of the primary coil, for example, the three-dimensionally arranged portion is first inserted into the aneurysm, and the spiral portion continuous from the circle corresponding to the portion formed by the small-diameter portion 333 to the tapered portion 334 of the mandrel 301 plays the role of an anchor in the aneurysm and is easy to fix to the aneurysm wall, thereby facilitating the insertion of the rest of the primary coil into the aneurysm.

After that, when the delivery wire 74 and the in vivo indwelling member 132 are decoupled by a standard method, the in vivo indwelling member 132 in the spatial three-dimensional cubic secondary shape (13, 130, 131, or 133) as illustrated in FIG. 7D, 8A, 11, or 15 indwells inside the aneurysm 71.

REFERENCE SIGNS LIST

10 Wire
11 and 11a Primary Coil
12, 120, and 121 Intermediate-shape coil
13, 130, 131, and 133 Secondary coil
14 Mandrel
20 Three-dimensional body
21 Loop part
21 a, 21 b, 21 c, and 21 d Segment
22 Cubic body
23a, 23b, 23c, and 23d Side surface of cubic body
24 Upper surface
24a Upper opening surface
25 Lower surface
25a Lower opening surface
26 Hollow portion
27 Central axis
30, 300, and 301 Mandrel
31 and 331 First three-dimensional body formation part
31a, 31b, 31c, and 31d First rod-shaped portion
32 and 332 Second three-dimensional body formation part
32a, 32b, 32c, and 32d Second rod-shaped portion
33 Additional three-dimensional body formation part
33a, 33b, 33c, and 33d Additional rod-shaped portion
35 Winding start position on first three-dimensional body formation part
38 Core wire
39 Core wire fixation position
40 One end
45 Additional three-dimensional body terminal end
51 and 351 First three-dimensional body
51a, 51b, 51c, and 51d Segment
52 and 352 Second three-dimensional body
52a, 52b, 52c, and 52d Segment
53 Additional three-dimensional body
53a, 53b, 53c, and 53d Segment
54, 540, and 354 Coupling element part
55 and 355 Upper opening surface of first three-dimensional body
56 and 356 Upper opening surface of second three-dimensional body
57 and 357 Central axis of opening surface of first three-dimensional body
58 and 358 Central axis of opening surface of second three-dimensional body
59 Plane
60 Regular square corresponding to first three-dimensional body
61 Regular square corresponding to second three-dimensional body
62 Vertex of regular square corresponding to first three-dimensional body
63 Vertex of regular square corresponding to second three-dimensional body
62a and 63a Line segment
68 Plane
71 Aneurysm
72 Parent blood vessel
73 Delivery catheter
74 Delivery wire
75 Inner cavity part
76 Tip opening
132 In vivo indwelling member
261, 262, 263, 326, and 327 Hollow portion
331a, 331b, 331c, and 331d First rod-shaped portion
332a, 332b, 332c, and 332d Second rod-shaped portion
351a, 351b, 351c, and 351d Segment
352a, 352b, 352c, and 352d Segment
α and β Angle

The invention claimed is:

1. A method for producing an in vivo indwelling member having a secondary coil in which a secondary shape is given to a linear primary coil with a primary shape given to a linear material, the method comprising:
a first three-dimensional spatial body formation step of forming a first three-dimensional spatial body, which defines a first polygonal cylindrical shape, by aligning in a loop a plurality of segments, each of the segments being formed by winding the primary coil at least once, so that said plurality of segments of the first three-dimensional spatial body are arranged to define the first polygonal cylindrical shape, wherein
the plurality of segments of said first polygonal cylindrical shape consist of four circular loops surrounding a central axis of said first polygonal cylindrical shape and each of said four circular loops comprising a loop opening, wherein the circular loops and the loop openings define sides of the first polygonal cylindrical shape, and the four circular loops are aligned to form said first polygonal cylindrical shape defining openings at a distal end and a proximal end on the central axis;
a second three-dimensional spatial body formation step of forming a second three-dimensional spatial body, which defines a second polygonal cylindrical shape, by aligning in a loop a plurality of segments, each of the segments being formed by winding the primary coil at least once, so that said plurality of segments of the second three-dimensional spatial body are arranged to define the second polygonal cylindrical shape, after the formation of the first three-dimensional spatial body, wherein
the plurality of segments of said second polygonal cylindrical shape consist of four circular loops surrounding a central axis of said second polygonal cylindrical shape and each of said four circular loops comprising a loop opening, wherein the circular loops and the loop openings define sides of the second polygonal cylindrical shape, and the four circular loops are aligned to form said second polygonal cylindrical shape defining openings at a distal end and a proximal end on the central axis; and an inside arrangement step of placing one of the first and second three-dimensional spatial bodies inside the other of the first and second three-dimensional spatial bodies through said opening at the distal end or the proximal end, after the first and second three-dimensional spatial body formation steps, such that i) the central axes of the adjacent three-dimensional spatial bodies are in a positional relationship of crossing or of a skew position, or ii) the central axes are concentric or parallel to each other.

2. The method for producing an in vivo indwelling member according to claim 1, wherein
the shapes of the polygonal cylindrical shapes of the first and second three-dimensional spatial bodies are the same and the size of the polygonal cylindrical shapes are the same or different among the three-dimensional spatial bodies with regard to the shapes recognized in a cross-sectional direction orthogonal to central axes of the cylindrical three-dimensional spatial bodies.

3. The method for producing an in vivo indwelling member according to claim 1, wherein the primary coil constituting the segments is arranged two-dimensionally or three-dimensionally.

4. The method for producing an in vivo indwelling member according to claim 1, wherein the segments are formed by winding the primary coil around a mandrel at least once.

5. The method for producing an in vivo indwelling member according to claim 4, wherein the mandrel is structured to have at least two connected parts with annular arrangement of rod-shaped portions around which the primary coil can be wound.

6. The method for producing an in vivo indwelling member according to claim 1, wherein each of said first and second polygonal cylindrical shapes is formed of the four circular loops that are each generally at right angles to each other.

7. The method for producing an in vivo indwelling member according to claim 1, wherein
before the inside arrangement step, the first and second three-dimensional spatial bodies are formed so that i) the opening at the distal of the first three-dimensional spatial body and the opening at the distal end of the second three-dimensional spatial body face in parallel each other, and ii) the opening at the proximal end of the first three-dimensional spatial body and the opening at the proximal end of the second three-dimensional spatial body faces in parallel to each other.

8. A method for producing an in vivo indwelling member having a secondary coil in which a secondary shape is given to a linear primary coil with a primary shape given to a linear material, the method comprising:
a first three-dimensional spatial body formation step of forming a first three-dimensional spatial body, which defines a first polygonal cylindrical shape, by aligning in a loop a plurality of segments, each of the segments being formed by winding the primary coil at least once, so that said plurality of segments of the first three-dimensional spatial body are arranged to define the first polygonal cylindrical shape, wherein
the plurality of segments of said first polygonal cylindrical shape consist of four circular loops surrounding a central axis of said first polygonal cylindrical shape and each of said four circular loops comprising a loop opening, wherein the circular loops and the loop openings define sides of the first polygonal cylindrical shape, and the four circular loops are aligned to form said first polygonal cylindrical shape defining openings at a distal end and a proximal end on the central axis;

a second three-dimensional spatial body formation step of forming a second three-dimensional spatial body, which defines a second polygonal cylindrical shape, by aligning in a loop a plurality of segments, each of the segments being formed by winding the primary coil at least once, so that said plurality of segments of the second three-dimensional spatial body are arranged to define the second polygonal cylindrical shape, after the formation of the first three-dimensional spatial body, wherein the plurality of segments of said second polygonal cylindrical shape consist of four circular loops surrounding a central axis of said second polygonal cylindrical shape and each of said four circular loops comprising a loop opening, wherein the circular loops and the loop openings define sides of the second polygonal cylindrical shape, and the four circular loops are aligned to form said second polygonal cylindrical shape defining openings at a distal end and a proximal end on the central axis;

a third three-dimensional spatial body formation step of forming a third three-dimensional spatial body, which defines a third polygonal cylindrical shape, by aligning in a loop a plurality of segments, each of the segments being formed by winding the primary coil at least once, so that said plurality of segments of the third three-dimensional spatial body are arranged to define the third polygonal cylindrical shape, after the formation of the first and second three-dimensional spatial bodies, wherein the plurality of segments of said third polygonal cylindrical shape consist of four circular loops surrounding a central axis of said third polygonal cylindrical shape and each of said four circular loops comprising a loop opening, wherein the circular loops and the loop openings define sides of the third polygonal cylindrical shape, and the four circular loops are aligned to form said third polygonal cylindrical shape defining openings at a distal end and a proximal end on the central axis;

a first inside arrangement step of placing one of the first, second and third three-dimensional spatial bodies inside one of the two remaining first, second and third three-dimensional spatial bodies through said opening at the distal end or the proximal end, after the first, second and third three-dimensional spatial body formation steps; and then a second inside arrangement step of placing the one remaining three-dimensional spatial body inside the three-dimensional spatial body, which is arranged innermost at the first inside arrangement step, or placing the two three-dimensional spatial bodies, through said opening at the distal end or the proximal end of the three-dimensional spatial body arranged innermost, after the first inside arrangement step inside the one remaining three-dimensional spatial body.

9. The method for producing an in vivo indwelling member according to claim 1 or 8, wherein one of the first and second polygonal cylindrical shapes of the three-dimensional spatial bodies is smaller than the other of the first and second three-dimensional spatial bodies and is arranged inside the other of the polygonal cylindrical shapes of the first and second three-dimensional spatial bodies.

10. A method for producing an in vivo indwelling member comprising a primary coil having a primary shape given to a linear material and a secondary coil having a secondary shape, the secondary shape of the secondary coil formed by the primary coil, the method comprising:

forming a plurality of first circular segments, each of said circular segments formed by winding a part of a primary coil at least once, and three-dimensionally aligning the plurality of the first circular segments to form a first three-dimensional spatial body, which defines a first polygonal cylindrical shape, so that the first three-dimensional spatial body has an inner space surrounded by the plurality of the first circular segments, wherein the plurality of first circular segments consist of four circular loops surrounding a central axis of said first polygonal cylindrical shape and each of said four circular loops comprising a loop opening, wherein the circular loops and the loop openings define sides of the first polygonal cylindrical shape, and the four circular loops are aligned to form said first polygonal cylindrical shape defining openings at a distal end and a proximal end on the central axis;

forming a plurality of second circular segments, each of said second circular segments formed by winding another part of the primary coil at least once, and three-dimensionally aligning the plurality of the second circular segments to form a second three-dimensional spatial body, which defines a second polygonal cylindrical shape, so that the second three-dimensional spatial body has an inner space surrounded by the plurality of the second circular segments, wherein the plurality of second circular segments consist of four circular loops surrounding a central axis of said second polygonal cylindrical shape and each of said four circular loops comprising a loop opening, wherein the circular loops and the loop openings define sides of the second polygonal cylindrical shape, and the four circular loops are aligned to form said second polygonal cylindrical shape defining openings at a distal end and a proximal end on the central axis; and after forming the first and second three-dimensional spatial bodies, placing one of the first and second three-dimensional spatial bodies within the inner space of the other of the first and second three-dimensional spatial bodies, through said opening at the distal end or the proximal end, so that the in vivo indwelling member is produced.

* * * * *